United States Patent [19]

Nishino et al.

[11] Patent Number: 5,756,505
[45] Date of Patent: May 26, 1998

[54] N-ACYLPIPERAZINE DERIVATIVE, ANTIBACTERIAL DRUG AND ANTI-ULCER DRUG

[75] Inventors: Chikao Nishino; Fumitaka Sato, both of Yokohama; Tomohiro Uetake, Tokyo; Hirotada Fukunishi, Yokohama; Nao Kojima, Tokyo; Koji Kobayashi, Yokohama, all of Japan

[73] Assignee: Shiseido Co., Ltd., Tokyo, Japan

[21] Appl. No.: 625,992

[22] Filed: Apr. 1, 1996

[30] Foreign Application Priority Data

Mar. 31, 1995 [JP] Japan .................. 7-100741

[51] Int. Cl.$^6$ .................. A61K 31/495; C07D 405/12; C07D 295/205
[52] U.S. Cl. .................. 514/253; 514/255; 544/377; 544/387; 544/391
[58] Field of Search .................. 544/377, 387, 544/391; 514/253, 255

[56] References Cited

U.S. PATENT DOCUMENTS 4,208,205  6/1980  Fawzi .................. 71/118

FOREIGN PATENT DOCUMENTS

| 0 416 410 A1 | 3/1991 | European Pat. Off. . |
| 0 497 740 A1 | 8/1992 | European Pat. Off. . |
| 57-149254 | 9/1982 | Japan . |
| 385 877 | 3/1965 | Switzerland . |

OTHER PUBLICATIONS

Subramanyam et al, Biorganic & Medicinal Chemistry Letters, 5, pp. 319–324 (Feb. 16, 1995).
Hodogaya Chemical Co., Chemical Abstracts, vol. 98, No. 71705 (1983).
Suter et al, Chemical Abstracts, vol. 67, No. 3099 (1967).
Valenta et al, Chemical Abstracts, vol. 103, No. 178015 (1985).
Sankyo Co., Chemical Abstracts, vol. 97, No. 216219 (1982).

Primary Examiner—Emily Bernhardt
Attorney, Agent, or Firm—Ronald R. Snider

[57] ABSTRACT

An N-acylpiperazine derivative or a salt thereof in accordance with the present invention is represented by the following formula 1:

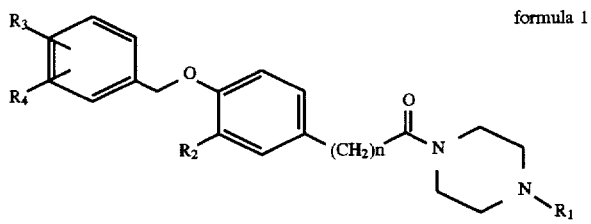

formula 1 wherein $R_1$ represents a lower alkyl, hydroxy lower alkyl, lower acyl, or arylcarbonyloxy lower alkyl group;

$R_2$ represents hydrogen atom or a lower alkyl, lower alkoxy, lower alkenyl, amino, or nitro group;

$R_3$ and $R_4$, which are identical to or different from each other, represent hydrogen atoms, halogen atoms, or cyano, nitro, lower alkyl, or lower alkoxy groups; and n represents 0 or 1.

The N-acylpiperazine derivative has anti-ulcer effect or an antibacterial activity against *Helicobacter pyroli* to be available for prevention or cure of ulsers.

24 Claims, 3 Drawing Sheets

REACTION FORMULA A;

REACTION FORMULA B;

REACTION FORMULA C;

REACTION FORMULA D;

REACTION FORMULA E;

REACTION FORMULA F;

REACTION FORMULA G;

REACTION FORMULA H;

N-ACYLPIPERAZINE DERIVATIVE, ANTIBACTERIAL DRUG AND ANTI-ULCER DRUG

RELATED APPLICATIONS

This application claims the priority if Japanese Patent Application No. 7-100741 filed on Mar. 31, 1995, which is incorporated herein by reference.

FIELD OF THE INVENTION

The present invention relates to an N-acylpiperazine derivative and, in particular, to an N-acylpiperazine derivative having an antibacterial activity against *Helicobacter pyroli* or anti-ulcer effect.

BACKGROUND OF THE INVENTION

Various theories have been proposed with respect to a cause of ulcer in human. In particular, it has been elucidated that stress, taking of non-steroidal anti-inflammatory drugs for curing rheumatic diseases, and the like are closely related to ulcer formation, mainly due to relatively excess gastric acid secretion. Accordingly, it is important to suppress the acid secretion in order to prevent ulcer formation and to cure it.

On the other hand, it has been considered that *Helicobacter pyroli* which is a rod normally existing in stomach, generates ammonia due to its strong urease activity, thereby inducing ulcer and persistence of itself. Since it persistently lives within mucus and mucosa, it becomes the greatest cause for recurrence of ulcer. Accordingly, it has been considered that the recurrence of ulcer can be prevented if this bacterium is sterilized.

Though various kinds of medicaments for curing ulcer have been conventionally developed, few medicaments have been known to have an effect for preventing stress ulcers from generating and an antibacterial activity against *Helicobacter pyroli*.

SUMMARY OF THE INVENTION

In view of the problems of the above-mentioned prior art, the object of the present invention is to provide a compound which is excellent in preventing ulcer from generating and to provide antibacterial drug against *Helicobacter pyroli* and anti-ulcer drug including such a compound as a main component.

As a result of the diligent studies conducted by the inventors, it has been found that a specific N-acylpiperazine derivative is effective against various kinds of ulcer due to its antibacterial property against *Helicobacter pyroli* or its acid secretion inhibition as a main action mechanism. Thus, the present invention has been accomplished.

Namely, an N-acylpiperazine derivative or a salt thereof in accordance with the present invention is characterized by the following formula 1:

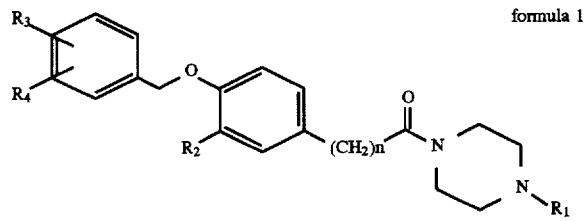

formula 1 wherein $R_1$ represents a lower alkyl, hydroxy lower alky, lower acyl, or arylcarbonyloxy lower alkyl group;

$R_2$ represents hydrogen atom or a lower alkyl, lower alkoxy, lower alkenyl, amino, or nitro group;

$R_3$ and $R_4$, which are identical to or different from each other, represent hydrogen atoms, halogen atoms or cyano, nitro, lower alkyl, or lower alkoxy groups; and n represents 0 or 1.

In the present invention, $R_1$ is preferably a branched lower alkyl group.

Also, in the present invention, $R_2$ is preferably a branched lower alkyl group.

More preferably, in the present invention, each of $R_1$ and $R_2$ is a branched lower alkyl group.

In the present invention, at least one of $R_1$ and $R_2$ is preferably isobutyl group.

More preferably, in the present invention, each of $R_1$ and $R_2$ is preferably isobutyl group.

In the present invention, at least one of $R_3$ and $R_4$ is preferably fluorine atom.

More preferably, said fluorine atom is bonded to para-position.

In the present invention, it is preferable that each of $R_1$ and $R_2$ is isobutyl group and $R_3$ is fluorine atom bonded to para-position.

An antibacterial drug against *Helicobacter pyroli* in accordance with the present invention is characterized by comprising, as an effective ingredient, said N-acylpiperazine derivative or the pharmacologically acceptable salt thereof, together with a pharmaceutically acceptable carrier and/or adjuvant.

An anti-ulcer drug in accordance with the present invention is characterized by comprising, as an effective ingredient, said N-acylpiperazine derivative or the pharmacologically acceptable salt thereof, together with a pharmaceutically acceptable carrier and/or adjuvant.

In said anti-ulcer drug, said pharmacologically acceptable salt is preferably a hydrochloride or an oxalate.

A method for the treatment of peptic ulcers in man or mammals in accrodance with the present invention is characterized by administration to a host of a therapeutically effective amount of said N-acylpiperazine derivative or the pharmacologically acceptable salt thereof.

In said method for treatment, said peptic ulcers are preferable gastric ulcers in man.

Also, a method for the inhibition of acid secretion in stomach of man or mammals in accordance with the present invention is characterized by administration to a host of a effective amount of said N-acylpiperazine derivative or the pharmacologically acceptable salt thereof.

A method for the inhibition of growth of *Helicobacter pyroli* in stomach of man or mammals in accordance with the present invention is characterized by administration to a host of a effective amount of said N-acylpiperazine derivative or the pharmacologically acceptable salt thereof.

A method for the prevention of peptic ulcers in man or mammals in accordance with the present invention is characterized by administration to a host of a preventively effective amount of said N-acylpiperazine derivative or the pharmacologically acceptable salt thereof.

In said method for prevention, said peptic ulcers are preferably gastric ulcers in man.

DETAILED DESCRIPTION OF THE INVENTION

In the following, the present invention will be explained in further detail.

In the compound of the present invention, the lower alkyl group found at $R_1$, and $R_2$ represents a straight or branched alkyl group having 1 to 6 carbon atoms. Examples thereof include methyl, ethyl, n-propyl, n-butyl, isopropyl, isobutyl, 1-methylpropyl, tert-butyl, n-pentyl, 1-ethylpropyl, isoamyl, and n-hexyl. In order to attain a stable anti-ulcer effect, a branched lower alkyl group is preferable and isobutyl group is particularly preferable.

The lower alkyl groups found at $R_3$ and $R_4$ can be exemplified by the above-mentioned groups. Preferably, they are methyl group.

In the definition of $R_2$, $R_3$, and $R_4$, the lower alkoxy group represents a group derived from the above-mentioned lower alkyl group. A preferable example thereof is methoxy group.

In the definition of $R_1$, the alkyl group in "hydroxy lower allyl group" can be exemplified by a straight alkyl group having 1 to 4 carbon atoms. A preferable example thereof is ethyl group.

In the definition of $R_1$, examples of the lower acyl group include acetyl, propionyl, butyryl, isobutyryl, and pivaloyl. A preferable example thereof is isobutyryl group.

In the definition of $R_1$, the aryl group in "arylcarbonyloxy lower alkyl group" represents a substituted or unsubstituted phenyl group. Preferably, it is 3,4-methylenedioxyphenyl group expressed by the following formula.

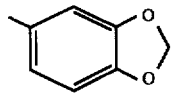

Also, the lower alkyl group in "arylcarbonyloxy lower alkyl group" can be examplified by a straight alkyl group having 1 to 4 carbon atoms and is preferably ethyl group.

The lower alkenyl group found at $R_2$ represents an alkenyl group having 3 to 4 carbon atoms. A preferable example thereof is isobutenyl group.

The halogen atom found at $R_3$ and $R_4$ represents chlorine, bromine, iodine, or fluorine. The most preferable example thereof is fluorine. This fluorine atom preferably exists at least at para-position, whereby the safety with respect to organisms can be remarkably increased.

While the compound of the present invention can be manufactured by the reaction formulas shown in FIGS. 1 to 4, it should not be restricted thereto.

First, in reaction formula A shown in FIG. 1, the N-acylpiperazine derivative of the present invention expressed by formula (I) can be obtained from the carboxylic acid expressed by formula (II) and the substituted piperazine expressed by formula (III), by using a known amide-bond forming reaction such as mixed anhydride method, acid chloride method, DCC method, or azide method,. Here, $R_1$ in the compound (III) and $R_2$, $R_3$, $R_4$, and n in the compound (II) are defined as mentioned above.

In the mixed anhydride method, by using an activator such as diphenyl phosphinic chloride, ethyl chloroformate, isobutyl chloroformate, or pivaloyl chloride, the carboxylic acid (II) is converted into its corresponding anhydride and then reacted with the compound (III). As an additive, for example, an organic base such as triethyl amine, pyridine, or N-methylmorpholine is used. As a solvent, for example, a halogenated hydrocarbon such as dichloromethane or chloroform; an aromatic hydrocarbon such as benzene, toluene, or xylene; an ether such as tetrahydrofuran or dioxane; or an amide such as N,N-dimethylformamide or N,N-dimethylacetamide is used. While the reaction temperature and reaction time may be changed according to the material compounds used, the reaction is usually effected at a temperature within the range of $-15°$ C. to the reflux temperature of the solvent.

In the acid chloride method, as an activator, for example, phosphorus pentachloride, phosphorus trichloride, or thionyl chloride is used to convert the carboxylic acid (II) into the corresponding acid chloride and then the latter is reacted with the compound (III). As an additive, for example, an organic base such as triethyl amine, pyridine, or N-methylmorpholine is used. As a solvent, for example, a halogenated hydrocarbon such as dichloromethane or chloroform; an aromatic hydrocarbon such as benzene, toluene, or xylene; or an amide such as N,N-dimethyl formamide or N,N-dimethylacetamide is used. While the reaction temperature and reaction time may be changed according to the material compounds used, the reaction is usually effected at a temperature within the range of $0°$ C. to the reflux temperature of the solvent.

In the DCC method, as a condensing agent, for example, N,N'-dicyclohexyl carbodiimide (DCC) or 1-ethyl-3-(3-dimethylaminopropyl)carbodiimide hydrochloride (EDCI) is used. As a solvent, for example, a halogenated hydrocarbon such as dichloromethane or chloroform; an aromatic hydrocarbon such as benzene, toluene, or xylene; an ether such as tetrahydrofuran or dioxane; or an amide such as N,N-dimethylformamide or N,N-dimethylacetamide is used. If necessary, this reaction may be effected while 1-hydroxybenzotriazole (HOBt) or N-hydroxy succinimide (HONSu) is added thereto. While the reaction temperature and reaction time may be changed according to the material compounds used, the reaction is usually effected at a temperature within the range of $0°$ C. to the reflux temperature of the solvent.

In the azide method, as an activator, for example, diphenylphosphorylazide is used to convert the carboxylic acid (II) into its corresponding azide and then the latter is reacted with the compound (III). As an additive, for example, an organic base such as triethylamine, pyridine, or N-methylmorpholine is used. As a solvent, for example, a halogenated hydrocarbon such as dichloromethane or chloroform; an aromatic hydrocarbon such as benzene, toluene, or xylene; or an amide such as N,N-dimethylformamide or N,N-dimethylacetamide is used. While the reaction temperature and reaction time may be changed according to the material compounds used, the reaction is usually effected at a temperature within the range of $0°$ C. to the reflux temperature of the solvent.

Specifically, for example, diphenylphosphinic chloride or pivaloyl chloride is used as an activator for the mixed anhydride method, while triethylamine is used as an additive to effect the reaction in a solvent such as chloroform or N,N-dimethyl formamide at a temperature within the range of $-15°$ C. to room temperature, thereby attaining the aimed object.

FIG. 2 shows reaction formula B.

At the first step of reaction formula B shown in this chart, the compound expressed by formula (V) can be obtained from the carboxylic acid expressed by formula (II) and the protected piperazine expressed by formula (IV), by using the condensation method described with reference to reaction formula A,. In the compound (II), $R_2$, $R_3$, $R_4$, and n are defined as mentioned above. In the compound (IV), $R_5$ represents an amino-protecting group which can be a urethane type protecting group such as benzyloxycarbonyl group or tert-butyloxycarbonyl group, an acyl type protecting group such as formyl group or tosyl group, or an alkyl type protecting group such as trityl group as long as no problem occurs in the subsequent reaction.

At the second step of reaction formula B, the compound expressed by formula (V) is subjected to a deprotecting reaction so as to obtain the compound expressed by formula (VI).

For this deprotecting reaction, various kinds of known methods can be used according to the kind of the amino-protecting group $R_5$. For example, hydrazine, hydrochloric acid, hydrogen peroxide, or the like can be used as the deprotecting agent when $R_5$ is formyl group. Specifically, for example, hydrochloric acid within the range of 1N to 6N is used in methanol to effect the reaction at a temperature within the range of 0° C. to room temperature, thereby attaining the aimed object.

At the third step in reaction formula B, the compound expressed by formula (VI) is reacted with the halide expressed by formula (VII) in the presence of a base, thereby yielding the N-acylpiperazine derivative expressed by formula (1) of the present invention. In the compound (VII), X represents a halogen atom.

When $R_1$ is a lower alkyl group or arylcarbonyloxy lower alkyl group, as a base, for example, an inorganic base such as potassium carbonate, potassium hydroxide, sodium hydroxide, or sodium hydride or an organic base such as triethylamine or pyridine is used. Specifically, for example, potassium carbonate is used as a base in a solvent such as acetone or N,N-dimethylformamide so as to effect a reaction at a temperature within the range of room temperature to the reflux temperature of the solvent, thereby attaining the aimed object.

Here, the compound (I) having an arylcarbonyloxy lower alkyl group as $R_1$ is further subjected to a common hydrolysis, thereby obtaining the compound (I) in which $R_1$ is a hydroxy lower alkyl group.

When $R_1$ is a lower acyl group, as a base, for example, an inorganic base such as potassium carbonate, potassium hydroxide, or sodium hydroxide, or an organic base such as triethylamine or pyridine is used. Specifically, for example, triethylamine or pyridine is used as a base in a solvent such as dichroromethane or benzene so as to effect a reaction at a temperature within the range of 0° C. to room temperature, thereby attaining the aimed object.

FIG. 3 shows reaction formula C.

At the first step of reaction formula C, the compound expressed by formula (IX) is obtained from the carboxylic acid expressed by formula (VII) and the substituted piperazine expressed by formula (III), by using the condensation method described with reference to reaction formula A. $R_1$ in the compound (III) and $R_2$ and n in the compound (VIII) are defined as mentioned above. $R_6$ in the compound (VII) represents a protecting group for a phenolic hydroxyl group. As long as no problem occurs in the subsequent reaction, benzyl group, various kinds of substituted benzyl groups, benzyloxycarbonyl group, tert-butyloxycarbonyl group, and the like can be used therefor.

At the second step of reaction formula C, the compound expressed by formula (IX) is subjected to a deprotecting reaction so as to obtain the compound expressed by formula (X).

For this deprotecting reaction, various kinds of known methods can be used according to the kind of the protecting group $R_6$. For example, when $R_6$ is benzyl group, reductive elimination method or acid-treated elimination method is used. Specifically, for example, under a catalytic reduction condition, by using palladium-carbon as a catalyst, a reaction is effected in a solvent such as ethanol under a hydrogen gas atmosphere at a temperature within the range of room temperature to the reflux temperature of the solvent, thereby attaining the aimed object.

At the third step of reaction formula C, the compound expressed by formula (X) is reacted with the appropriately substituted benzyl halide expressed by formula (XI) in the presence of a base so as to obtain the N-acylpiperazine derivative of the present invention expressed by formula (I). In the compound (XI), $R_3$ and $R_4$ are defined as mentioned above, while X represents a halogen atom.

As a base in this reaction, for example, an inorganic base such as potassium carbonate, potassium hydroxide, sodium hydroxide, or sodium hydride, or an organic base such as triethylamine or pyridine is used. Specifically, for example, potassium carbonate is used as a base in a solvent such as acetone or N,N-dimethylformamide so as to effect a reaction at a temperature within the range of room temperature to the reflux temperature of the solvent, thereby attaining the aimed object.

FIG. 4 shows reaction formula D.

In reaction formula D, the compound (I-a), which has nitro group as $R_2$ in the formula (I) in reaction formulas A to C, is reduced so as to obtain the compound (I-b) in which $R_2$ is amino group in formula (I). In the compound (I-a), $R_1$, $R_3$, $R_4$, and n are defined as mentioned above.

Examples of the reducing agent in this reaction include zinc, aluminum, tin, tin (II) chloride, iron, palladium, platinum, rhodium, and nickel. Specifically, for example, by using an excess amount or, preferably, 3 to 7 equivalents amount of tin (II) chloride, the reaction is effected in a solvent such as ethanol at the reflux temperature of the solvent, thereby attaining the aimed object.

When the compound of the present invention expressed by formula (I) or (I-b) synthesized by the above-mentioned reaction formula A to D is reduced with a reducing agent such as lithium aluminum hydride, a compound in which carbonyl group of the amide bond is reduced to methylene group can be obtained.

The material compound expressed by formula (II) in reaction formulas A and B can be synthesized by reaction formula E.

FIG. 5 shows reaction formula E.

At the first step of reaction formula E, the compound expressed by formula (XII) is reacted with the appropriately substituted benzyl halide expressed by formula (XI) in the presence of a base to obtain the compound expressed by formula (XIII). $R_2$ and n in the compound (XII) and $R_3$ and $R_4$ in the compound (XI) are defined as mentioned above, while X in the compound (XI) represents a halogen atom. In the compound (XII), $R_7$ represents a carboxyl-protecting group which may be a lower alkyl group such as methyl group, ethyl group, or tert-butyl group, phenacyl group, trichloroethyl group, or the like as long as no problem occurs in the subsequent reaction.

As a base in this reaction, for example, an inorganic base such as potassium carbonate, potassium hydroxide, sodium hydroxide, or sodium hydride, or an organic base such as triethylamine or pyridine is used. Specifically, for example, potassium carbonate is used as a base in a solvent such as acetone or N,N-dimethylformamide so as to effect a reaction at a temperature within the range of room temperature to the reflux temperature of the solvent, thereby attaining the aimed object.

At the second step of reaction formula E, the compound expressed by formula (XIII) is subjected to a deprotecting reaction so as to obtain the carboxylic acid expressed by formula (II).

For this deprotecting reaction, various kinds of known methods can be used according to the kind of the protecting group $R_7$. For example, when $R_7$ is methyl or ethyl group, known ester hydrolysis method is used for deprotection. Specifically, for example, an inorganic base such as sodium hydroxide or potassium hydroxide is used so as to effect a reaction in a solvent such as water, methanol, or ethanol at a temperature within the range of room temperature to the reflux temperature of the solvent, thereby attaining the aimed object.

In reaction formula E, the material compound expressed by formula (XII) may be commercially available or the compound (XII-a) in which $R_2$ is a lower 2-alkenyl group in formula (XII) can be synthesized by reaction formula F. Further, from the latter compound, the compound (XII-b) in which $R_2$ is a lower alkyl in formula (XII) can be prepared by reaction formula G.

FIG. 6 shows reaction formula F.

At the first step of reaction formula F, the compound expressed by formula (XIV) is reacted with the halide expressed by formula (XV) in the presence of a base so as to obtain the compound expressed by formula (XVI). In the compound (XIV), n is defined as mentioned above. In the compound (XV), $R_8$, $R_9$, $R_{10}$, $R_{11}$, and $R_{12}$ represent hydrogen atom or a lower alkyl group, while X represents a halogen atom. In the compound (XIV), $R_7$ represents a carboxyl-protecting group which may be a lower alkyl group such as methyl group, ethyl group, or tert-butyl group, phenacyl group, trichloroethyl group, or the like as long as no problem occurs in the subsequent reaction.

As a base in this reaction, for example, an inorganic base such as potassium carbonate, potassium hydroxide, sodium hydroxide, or sodium hydride, or an organic base such as triethylamine or pyridine is used. Specifically, for example, potassium carbonate is used as a base in a solvent such as acetone or N,N-dimethylformamide so as to effect a reaction at a temperature within the range of room temperature to the reflux temperature of the solvent, thereby attaining the aimed object.

At the second step of reaction formula F, the compound expressed by formula (XVI) is subjected to Claisen rearrangement reaction so as to obtain the compound expressed by formula (XII-a).

This reaction is effected in or without the presence of a high-boiling solvent under normal or high pressure. Examples of the high-boiling solvent include phenyl ether and N,N-dimethylaniline. While the reaction temperature and reaction time may be changed according to the material compounds used, the reaction is normally effected at a temperature within the range of 100° to 200° C.

FIG. 7 shows reaction formula G.

In reaction formula G, the compound expressed by formula (XII-b) can be obtained by hydrogenation of the compound expressed by formula (XII-a). In the compound (XII-a), n is defined as mentioned above, while $R_8$, $R_9$, $R_{10}$, $R_{11}$, and $R_{12}$ represent hydrogen atom or a lower alkyl group. Also, $R_7$ represents a carboxyl-protecting group which may be a lower alkyl group such as methyl, ethyl, or tert-butyl group, phenacyl group, trichloroethyl group, or the like as long as no problem occurs in the subsequent reaction.

When this reaction is effected under a catalytic reduction condition, as a catalyst, palladium, platinum, nickel, rhodium, ruthenium, or the like can be used. Specifically, for example, by using palladium-carbon, in a solvent such as ethanol, ethyl acetate, or tetrahydrofuran, under a hydrogen gas atmosphere, a reaction is effected at a temperature within the range of room temperature to the reflux temperature of the solvent, thereby attaining the aimed object.

The material compound expressed by formula (III) in reaction formula A or C can be commercially available or synthesized by reaction formula H.

FIG. 8 shows reaction formula H.

At the first step of reaction formula H, the protected piperazine expressed by formula (IV) is reacted with the appropriate halide expressed by formula (VII) in the presence of a base so as to obtain the compound expressed by formula (VII). In the compound (IV), $R_5$ represents an amino-protecting group which can be a urethane type protecting group such as benzyloxycarbonyl group or tert-butyloxycarbonyl group, an acyl type protecting group such as formyl group or tosyl group, or an alkyl type protecting group such as trityl group as long as no problem occurs in the subsequent reaction. In the compound (VII), X represents a halogen atom.

When $R_1$ is a lower alkyl group or arylcarbonyloxy lower alkyl group, as a base, for example, an inorganic base such as potassium carbonate, potassium hydroxide, sodium hydroxide, or sodium hydride or an organic base such as triethylamine or pyridine is used. Specifically, for example, potassium carbonate is used as a base in a solvent such as acetone or N,N-dimethylformamide so as to effect a reaction at a temperature within the range of room temperature to the reflux temperature of the solvent, thereby attaining the aimed object.

Here, the compound (XVII) having an arylcarbonyloxy lower alkyl group as $R_1$ is further subjected to a common hydrolysis, thereby obtaining the compound (XVII) in which $R_1$ is a hydroxy lower alkyl group.

When $R_1$ is a lower acyl group, as a base, for example, an inorganic base such as potassium carbonate, potassium hydroxide, or sodium hydroxide, or an organic base such as triethylamine or pyridine is used. Specifically, for example, triethyl amine or pyridine is used as a base in a solvent such as dichroromethane or benzene so as to effect a reaction at a temperature within the range of 0° C. to room temperature, thereby attaining the aimed object.

At the second step of reaction formula H, the compound expressed by formula (XVII) is subjected to a deprotecting reaction so as to obtain the compound expressed by formula (III).

For this deprotecting reaction, various kinds of known methods can be used according to the kind of the amino-protecting group $R_5$. For example, hydrazine, hydrochloric acid, hydrogen peroxide, or the like can be used as the deprotecting agent when $R_5$ is formyl group. Specifically, for example, hydrochloric acid within the range of 1N to 6N is used in methanol to effect the reaction at a temperature within 0° C. to room temperature, thereby attaining the aimed object.

Among the material compounds used in the above-mentioned reaction formulas, those with no preparation methods described, namely, the compounds (IV), (VII), (VIII), (XI), (XIV), and (XV) may be commercially available or easily synthesized by using a known method.

Also, examples of salts of the N-acylpiperazine derivative of the present invention expressed by formula (I) with an acid include salts with inorganic acids such as hydrochloric acid, hydrobromic acid, sulfuric acid, and phosphoric acid and salts with organic acids such as acetic acid, propionic acid, citric acid, lactic acid, oxalic acid, maleic acid, fumaric acid, succinic acid, tartaric acid, and methane sulfonic acid. These salts can be easily manufactured by a normal method.

The N-acylpiperazine derivative in accordance with the present invention has a strong effect against stress ulcer and an excellent effect for suppressing gastric acid secretion. Further, it has an antibacterial activity against *Helicobacter pyroli* which is supposed to be a cause for recurrence of ulcer. Furthermore, it has a high safety. Accordingly, it is useful as a medicament for curing and preventing peptic ulcer. Conventionally, there has hardly been known such a compound which has both effect for suppressing gastric acid secretion and antibacterial activity against *Helicobacter pyroli*. Accordingly, it is indicated that the compound of the present invention is not only effective in preventing and curing ulcer but also in preventing the recurrence thereof.

When the compound of the present invention is administered as a medicament for curing and preventing peptic ulcer, it may be administered orally as tablet, powder, granule, capsule, syrup, or the like as well as parenterally as suppository, injection, external drug, instillation or the like. While the amount of administration may be outside of the range mentioned below according to the degree of symptom, personal difference, age, kind of ulcer, or the like, it should of course be adjusted so as to fit the individual circumstances in specific cases. Usually 0.01 to 200 mg/kg or, preferably, 0.05 to 50 mg/kg or, more preferably, 0.1 to 10 mg/kg is administered per day for an adult in a single dose or several doses.

When formulating the medicament, a normal manufacturing method is used with a normal formulation carrier. If necessary, pharmacologically and pharmaceutically acceptable additives may be added thereto.

Namely, when preparing an oral solid formulation, after an excipient and, if necessary, a binder, a decaying agent, a luster, a coloring agent, a correctives, and the like are added to the main medicament, a normal method is used to form tablet, coated tablet, granule, powder, capsule, or the like.

Examples of the excipient include lactose, corn starch, sucrose, glucose, sorbitol, crystalline cellulose, and silicon dioxide. Examples of the binder include polyvinylalcohol, polyvinylether, ethyl cellulose, methyl cellulose, gum arabic, tragacanth, gelatin, shellac, hydroxypropyl cellulose, hydroxypropyl starch, and polyvinylpyrrolidone. Examples of the decaying agent include starch, agar, gelatin powder, crystalline cellulose, calcium carbonate, sodium hydrogencarbonate, calcium citrate, dextrin, and pectin. Examples of the luster include magnesium stearate, talc, polyethyleneglycol, silica, and hardened vegetable oil. As the coloring agent, those permitted to be added to medicines are used. Examples of the correctives include cocoa powder, menthol, aromatic acid, mentha oil, borneol, and cinnamon powder. If necessary, these tablet and granule can be coated with sugar-coating, gelatin-coating, and the like.

When preparing an injection, if necessary, a pH-adjusting agent, a buffer, a stabilizer, a solubilizer, and the like are added to the main medicament and then a normal method is used to form subcutaneous, intramuscular, and intravenous injection drugs.

EXAMPLES

Figure 1:
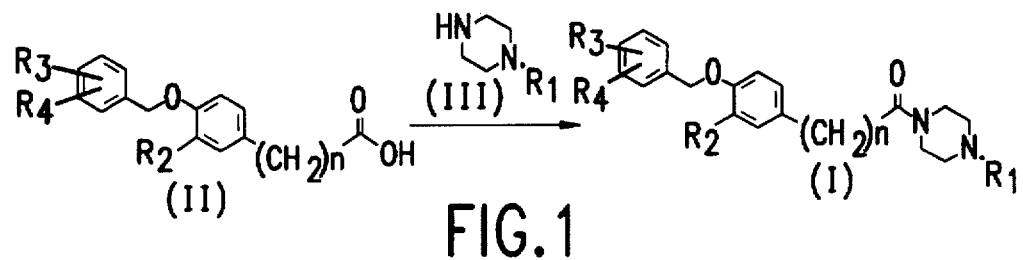
FIGS. 1 to 4 shows examples of steps for manufacturing the N-acylpiperazine derivative in accordance with the present invention and FIGS. 5 to 8 shows examples of steps for manufacturing material compounds for synthesizing the N-acylpiperazine derivative in accordance with the present invention.
Figure 2:
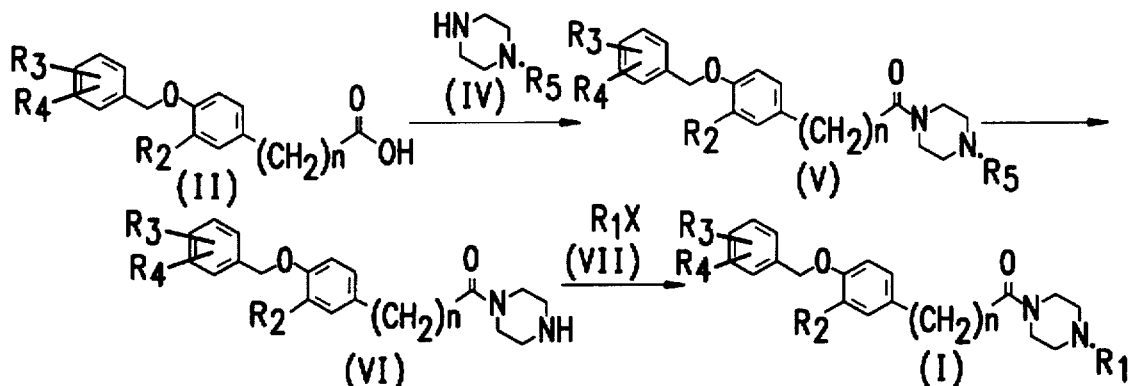
Figure 3:
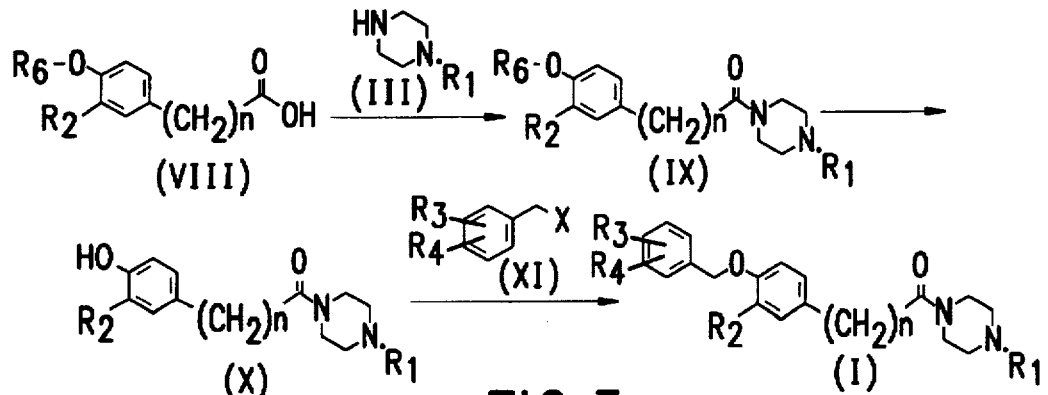
Figure 4:
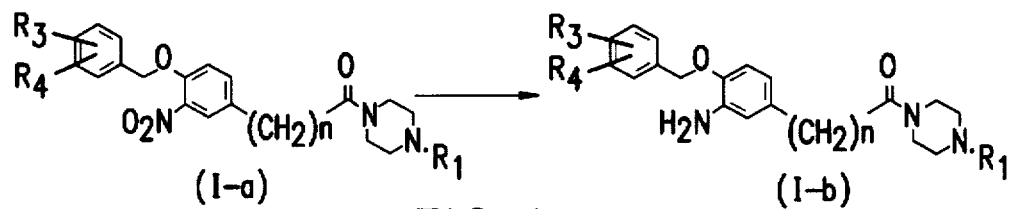
Figure 5:
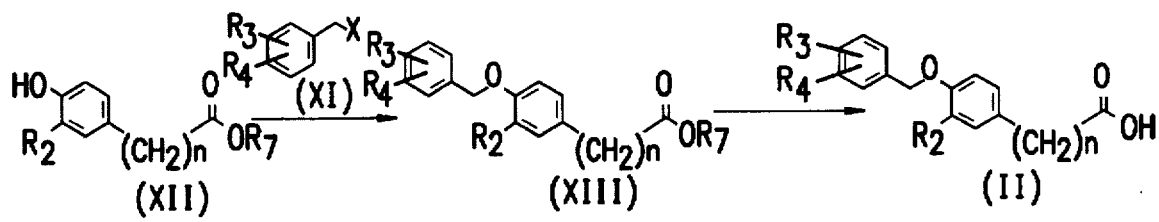
Figure 6:
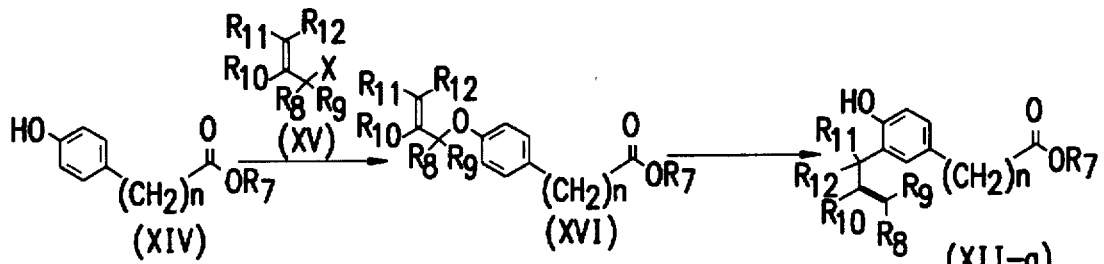
Figure 7:
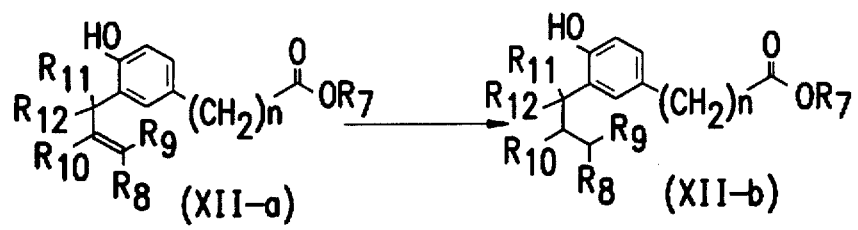
Figure 8:
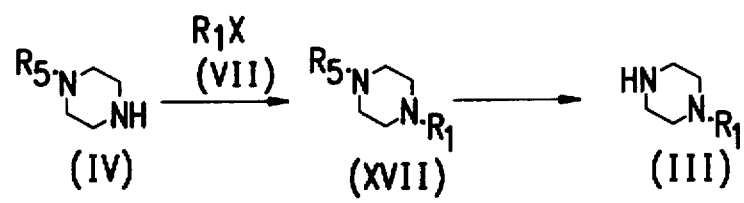

In the following, examples of the present invention will be explained in detail. However, the present invention should not be restricted to these examples.

First, test methods used for evaluating these examples as anti-ulcer drug will be explained.

WIS: Restraint and Water Immersion Stress-Induced Ulcer Inhibition Test
 i)Meaning
 The degree of inhibition of the stress ulcer formation is tested.
 ii)Method
 Male Crj:SDor Slc:SD rats (6 to 7-week-old) were fasted overnight, but allowed free access to water. Each group has 5 to 8 of these rats. The sample compound was dissolved or suspended in an aqueous solution of 0.3% sodium carboxymethylcellulose or 0.05% Tween 80 and then was orally administered (100 mg/10 ml/kg). To a control group, the vehicle was administered. 10 minuts later, the rats were placed in a stress cage and immersed to the level of xipfoid process in a water bath (21° C.) for 7 hours. At the end of the stress, the rats were sacrificed by inhalation of ether or carbon dioxide. Then, the stomach of each was removed, inflated by injecting 10 ml of 5% formalin neutral buffer solution, and immersed in 1% formalin neutral buffer solution for 30 minutes or more to be fixed. The stomach was incised along the greater curvature and then the length of each erosion in the glandular portion was determined under dissecting microscope. The sum of the length of erosions per stomach was defined as ulcer index (UI).
 iii)Judgment Standard
 The effect obtained when 100 mg/kg of the sample compound had been administered was expressed as ulcer formation inhibitory rate (%) as follows:
 ulcer formation inhibitory rate (%)=[1-(UI in sample group/UI in control group)]×100

VOL, TAO: Acid Secretion Inhibition Test In Vivo
 i)Meaning
 Inhibitory effect on acid secretion in vivo is confirmed.
 ii)Method
 Male Crj:Donryu rats (7-week-old) were fasted overnight but allowed free access to water. In each group, 8 to 10 of these rats were used under urethane anesthesia (1.25 g/kg). The sample compound dissolved or suspended in an aqueous solution of 0.5% sodium carboxymethylcellulose or 0.05% Tween 80 was orally administered (100 mg/10 ml/kg). 30 minutes later, the abdomen of each was incised and the pylorus was ligated. 30 minutes after the ligation, 30 mg/kg of histamine dissolved in physiological saline were subcutaneously administered and, 3 hours thereafter, the rat was sacrificed with carbon dioxide. Immediately thereafter, each stomach was removed and the gastric contents were collected and each volume was determined. The total acid output was determined by titration of the gastric juice with 0.1N NaOH.
 iii)Judgment Standard
 With respect to the gastric juice volume (VOL) and the total acid output (TAO), the effects obtained when 100 mg/kg of the sample compound had been administered were expressed as their respective inhibitory rates (%) as follows:
 each inhibitory rate (%)=[1-(value in sample group/value in control group)]×100

CAP: Acid Secretion Inhibition Test In Vitro i) Meaning

The acid secretion inhibitory activity in a cell level is studied. It can also be used for studying the mechanism of the effect.

ii) Method ii-a) Preparation of isolated gastric fundus gland suspension

First, an isolated gastric fundic gland sample was prepared. Namely, a male Japanese White rabbit (2.5 to 3 kg) was anesthetized to death with Nembutal™ and then the abdomen was incised. Immediately thereafter, the stomach was removed and, after its pyloric and cardiac antrum were severed, incised along its greater curvature into two sheets. The gastric contents adhering to the mucosal surface was washed out with ice-cooled PBS (−) and then carefully washed therein. The gastric wall was spread on a cork board with its mucosal surface facing up and the feed and mucus thereon were completely removed with sterile gauze. The mucosa was separated therefrom by a spatula and then collected in ice-cooled PBS (−). After being washed twice with PBS (−), the mucosa was minced into 2–3mm$^3$ pieces by scissors. These pieces were further washed twice with a nutrient solution. The nutrient solution comprises 132.4 mM of NaCl, 5.4 mM of KCl, 5 mM of $Na_2HPO_4 \cdot 12H_2O$, 1 mM of $NaH_2PO_4 \cdot 2H_2O$, 1.2 mM of $MgSO_4$, 1 mM of $CaCl_2$, 25 mM of HEPES, 2mg/ml of glucose, and 1 mg/ml of BSA. Into 70 ml of the nutrient solution containing 1 mg/ml of collagenase, minced mucosal pieces were dispersed and intensely stirred in a conical flask with a stirrer at 37° C. for 40 to 60 minutes. During this period, 100% $O_2$ was sprayed on the nutrient solution surface and the pH was appropriately measured such that it was immediately adjusted to pH 7.4, when the value was therebelow, with a base. The nutrient solution was added to the reaction solution so as to attain the total amount of about 200 ml. After being filtered through a mesh, the suspension was divisionally introduced into 50 ml centrifuge tubes and left for 15 minutes such that gastric fundic gland was deposited. The supernatant was repeatedly removed by an aspirator, dispersed in the nutrient solution, and then left such that the gastric fundic gland was washed three times. At this time, without using a pipette, the suspension was alternately introduced into two centrifuge tubes so as to effect dispersion. The number of cells was counted under microscope and adjusted to $1.6 \times 10^6$ cells/ml.

ii-b) [$^{14}$C]-aminopyrine uptake test

Then, [$^{14}$C]-aminopyrine uptake test was performed. After an Eppendorf tube was weighed, 10 µl (final concentration: $10^{-5}$M) of histamine dissolved in the above-mentioned nutrient solution, 10 µl (final concentration: $10^{-5}$M) of the test compound dissolved in DMSO, and 10 µl (final concentration: 0.05 µCi/ml) of [$^{14}$C]-aminopyrine diluted with the nutrient solution were introduced therein and then 970 µl of the isolated gastric fundic gland suspension prepared above were added thereto. Subsequently, this mixture was shaken at 37° C. for 40 minutes at 125 cycles/minute. After being centrifuged for 30 minutes 200 µl of its supernatant was collected into a mini-vial, while the rest was removed by an aspirator. The gland pellet was completely dried as the tube with its lid being opened was kept for one night in a drying oven at 80° C. and then the lid was closed and the weight was determined at room temperature. Then 100 µl of 1N KOH were added thereto and the tube with its lid being closed was treated at 60° C. for 1 to 2 hours so as to dissolve the pellet. Then, the contents thereof were transferred to a mini-vial. Into the mini-vial containing the supernatant or gland pellet, 4 ml of Atomlite™ were added and then the radioactivity was measured by a liquid scintillation counter. Here, after the radioactivity of the gland pellet was corrected by using a sample in which 20 mM of NaSCN were added so as to cancel the hydrogen ion concentration gradient, the integration ratio of aminopyrine specifically trapped by the gland pellet was calculated. This experiment was performed in duplicate.

ii-c) Computing of the accumulation rate of aminopyrine

Here, its principle will be briefly explained. In the isolated gastric fundic gland, acid is accumulated in a space between its secretory tubule and intraglandular cavity. Aminopyrine is weak base (pKa=5.0) and nonionic in a neutral solution so as to freely pass through the cell membrane, whereas it is ionized in an acidic solution and thus cannot pass through the cell membrane due to its electric charge. Therefore, aminopyrine is accumulated in a closed acidic space within the isolated gastric fundic gland. In view of this characteristic, the accumulation rate (R) of aminopyrine is computed by the following equation:

$$R = [(\text{corrected radioactivity of precipitate})/(\text{radioactivity of supernatant})] \times [200/(\text{mg dry weight of gland pellet})]$$

iii) Judgment Standard

The effect of the sample compound at the final concentration of $10^{-5}$ M was expressed by acid secretion inhibitory rate (%) as follows:

acid secretion inhibitory rate (%)=[1-(R in sample group/R in control group)]×100

AHP: Antibacterial Activity Test Against *Helicobacter pyroli* i) Meaning

The minimum inhibitory concentration (MIC) against *Helicobacter pyroli* (microaerophilic gram-negative bacterium which is supposed to deeply involve in pathogenesis, relapse, and recrudescence of ulcer, referred to as "HP" in the following) is measured so as to find out compounds which have antimicrobial activity against *Helicobacter pyroli*.

ii) Method

MICs were determined by the agar dilution method. The stock culture (−80° C.) of MP NCTC 11637 was thawed and cultured on tripticase soy agar supplemented with 5% sheep blood at 37° C. in an atmosphere of 5% $O_2$, 10% $CO_2$, and 85%$N_2$. Grown colonies were transfered to the same plate and cultured for 3 days under the same condition. An appropriate amount of the colony grown on the plate was suspended in Mueller Hinton broth till turbidity was recognizable by naked eyes, and diluted 100-fold in the same broth; this resulted in a suspension containig about $10^5$ cfu/ml.

A 1,000 µg/ml solution of the sample compound containing DMSO not more than 25% was seriesily diluted 2-fold in sterile purified water. 100 µl volume from each dilution was mixed thoroughly with 900 µl of brucella agar supplemented with 5% horse blood and solidified in a 24 well micro plate. 10 µl of the bacterial suspension (about $10^3$ cfu) was inoculated on this plate and cultured for 7 days under the same condition as that of preculture. Thereafter, it was judged whether there had been bacteria growth or not.

iii) Judgment Standard

The minimum concentration of the sample compound when there were no visible colonies or, if any, 5 or less colonies of HP was defined as MIC (µg/ml).

PD: Gastric Mucosal Integrity Test i) Meaning

There is a possibility that the anti-ulcer mechanism of the compounds which were effective in the experimental ulcer model may be attributed to adaptive cytoprotection, which means exhibiting of apparent anti-ulcer effect due to increase in the amount of endogeneous prostaglandins in the gastric mucosa caused by necrotizing agents. In this case, since the sample compound has a necrotizing effect, it is inappropriate as an anti-ulcer medicament.

Therefore, the gastric mucosal potential difference (PD), which reflects the integrity of the gastric mucosa, is measured so as to confirm that the sample compound has no damasing effect on gastric mucosa, which is toxicity at gastric mucosal level.

ii) Method

Male Crj:SD rats (7 to 8-week-old) was fasted overnight, but allowed free access to water, and then, under urethane anesthesia (1.25 g/kg, i.p.), fixed to a cork board on its back. The abdomen of each rat was incised, and a small incision was made in the forestomach. Then, the inside of the stomach was washed with physiological saline heated at 37° C. From the forestomach, along the greater curvature thereof, the stomach was incised without damaging blood vessels. After the height of the cork board was adjusted on a jack, the stomach was mounted on ex vivo chamber. The area of the gastric mucosa exposed to the inside of this chamber was 2.5 $cm^2$. The inside of the chamber was perfused with physiological saline warmed at 37° C. by micro tube pump. By using an agar bridge containing 3M KCl, the potential difference between the chamber and the abdominal cavity was measured by a PD meter. Here, the rectal temperature was measured to control the body temperature during the experiment. After the PD was sufficiently stabilized, the perfusate was stopped and then 100 mg/10 ml/kg of the sample compound dissolved or suspended in an aqueous solution of 0.5% sodium carboxymethyl cellulose or 0.05% Tween 80 were administered into the chamber, while PD was recorded for 60 minutes. To a control, the vehicle was administered.

iii) Judgment Standard

The change in PD during 60 minutes after the administration of 100 mg/kg of the sample compound was collectively studied and, with reference to the positive control, classified into 5 levels as follows:

5: Same as the control with no recognizable damage at all.

4: Though a slight PD-decreasing tendency suggesting a slight possibility of mucosal damage is found, there is no problem.

3: Though a weak decrease in PD and a possibility of a weak mucosal damage is recognized, there is no substantial problem.

2: Medium degree of decrease in PD is found and a mucosal damage is recognized.

1: Heavy degree of decrease in PD is found and a remarkable mucosal damage is recognized.

AT: Single Dose Toxicity Pretest ii) Method

Male Slc:ICR mice (5-week-old) were used. Each group has 3 to 5 mice and each mouse was fasted, but allowed free access to water, for 4 to 5 hours from 9 a.m. in the test day. Then, 2,000 mg/10 ml/kg of the sample compound dissolved or suspended in an aqueous solution of 0.5% sodium carboxymethylcellulose were orally administered thereto. To a control, only the vehicle was administered. The behavior and symptom were observed at each of 15 minutes, 30 minutes, 1 hour, 2 hours, and 3 hours after the administration and then daily till one week thereafter. The body weight was measured before and after the fasting as well as at the same time everyday. The dead animals were immediately subjected to autopsy and their organs were observed macroscopically. Also, the living animals were sacrificed with ether or carbon dioxide one week after the administration and then their organs were observed macroscopically.

iii) Judgment Standard

The toxicity at the single dose of 2,000 mg/kg of the sample compound was expressed as being classified into 5 levels.

5: Mortality rate is 0%; no toxicity is found at all both in behavior and organs.

4: Mortality rate is 0%; while no toxicity is found in organs, slight toxicity is observed in behavior and body weight increase.

3: While there is a dead animal (though not all the animals are dead), no toxicity is found in organs.

2: Regardless of whether there is a dead animal or not, toxicity is found in organs.

1: All the animals are dead.

MTT: Cell Damaging and Protecting Effect Test i) Meaning

It is confirmed that there is no toxicity in cell level. Those having a toxicity in cell level are inappropriate as an anti-ulcer drug. Also, it can be confirmed that the effects of the sample compounds in other cell level tests do not result from their toxicity.

ii) Method

A male Japanese White rabbit (2.5 to 3 kg) was anesthetized to death by Nembutal™ and, immediately thereafter, its stomach was removed. The greater curvature of the stomach was incised so as to remove the stomach contents therefrom. After the mucosal surface was washed with HBSS (Hanks' Balanced Salt Solution), the stomach in ice-cooled HBSS was transferred to a laboratory. Then, after the pyloric antrum was removed, the gastric corpus mucosa was separated by a spatula and then minced into 2 to 3 $mm^3$ pieces in BME (Basal Medium Eagle). Thereafter, these pieces were shaken at 120 to 130 cycles/minute for 15 minutes at 37° C. in BME 60ml containig 280 U/ml of dispase and 30 to 50 U/ml of collagenase. Here, the concentration of collagenase was appropriately changed for each lot in view of the state of cells. The pieces were washed twice with EBSS (Earle's Balanced Salt Solution) containing 1 mM of EDTA and then shaken in MEM (Minimum Essential Medium) containing 1 mM of EDTA at 37° C. for 5 minutes. Subsequently, they were shaken in the dispase and collagenase having the same concentrations as those mentioned above for 15 minutes so as to remove the supernatant and then further shaken at 37° C. for 50 to 60 minutes at 120 to 130 cycles/minute. Then, after being washed twice with HBSS, Ham F12 containing 2% of Ultrocer G™ was used to attain the concentration of $1 \times 10^6$ cells/ml. Thus formed suspension was dispensed in each well of a 96-well plate by 200 µl. The plate was incubated in the atmosphere composed of 5% $CO_2$ and 95% air at 37° C. for three days so as to attain a confluent state and then subjected to MTT assay.

The sample compound was dissolved in DMSO so as to attain a concentration of $10^{-2}$ M and then diluted with HBSS containing 2% of Ultrocer G™ so as to attain a final concentration of $10^{-4}$ M. To each group, which 8 wells were used for, 10 µl of MTT reagent were added immediately after 100 µl of the medium in each well were exchanged for same volume of the resulting solution of the sample compound. After being incubated in an atmosphere composed of 5% $CO_2$ and 95% air at 37° C. for 4 hours, thus formed solution was centrifuged and then its supernatant was discarded. Subsequently, 100 μl of 100% ethanol were added to the residue so as to dissolve MTT formazan. Then, the absorbance (OD: 570 to 630) was measured by a microplate reader. This method utilizes a phenomenon in which MTT is changed to MTT formazan only by mitochondria of living cells so as to change color.

iii)Judgment Standard

The cell damaging or cell protecting effect of the sample compound at the final concentration of $10^{-4}$ M was expressed as cell damaging rate (%) as follows:

cell damaging rate (%)=[1-(absorbance in sample group/absorbance in control group)]×100

Accordingly, the smaller value is better in the cell damaging rate.

Based on the foregoing effect tests and safety tests, the anti-ulcer effect, antibacterial activity against HP, and safety of the example compounds of the present invention were studied.

COMPOUND GROUP 1

As the N-acylpiperazine derivatives corresponding to this group, the following compounds of Examples 1 to 10 were tested. The results of their effect tests and safety tests are shown in Table 1.

Example 1

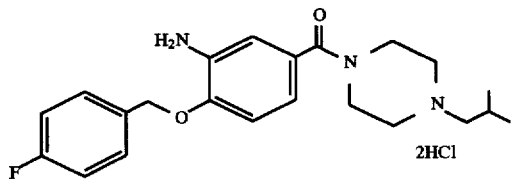

Example 2

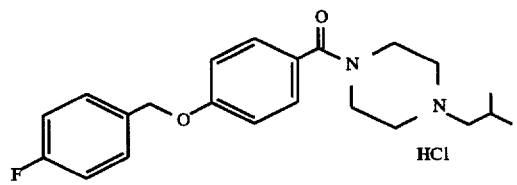

Example 3

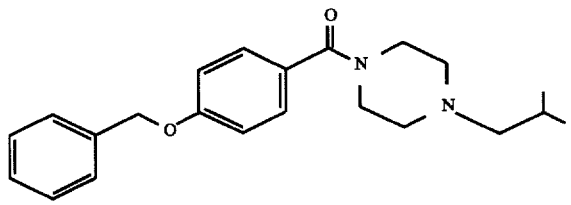

Example 4

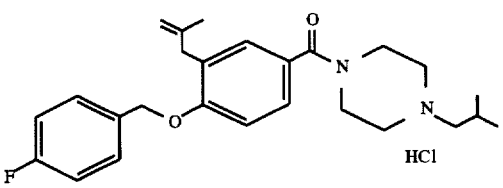

Example 5

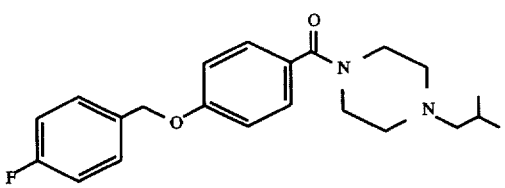

Example 6

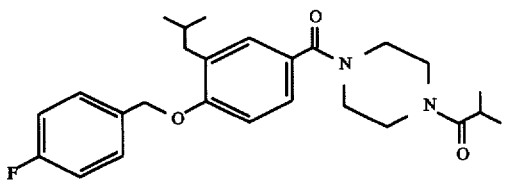

Example 7

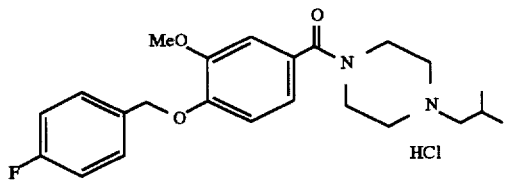

Example 8

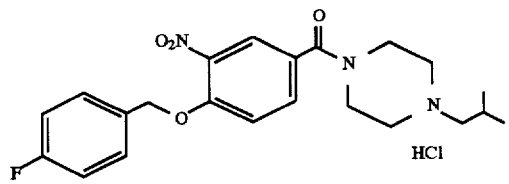

Example 9

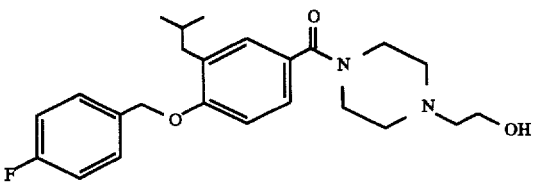

Example 10

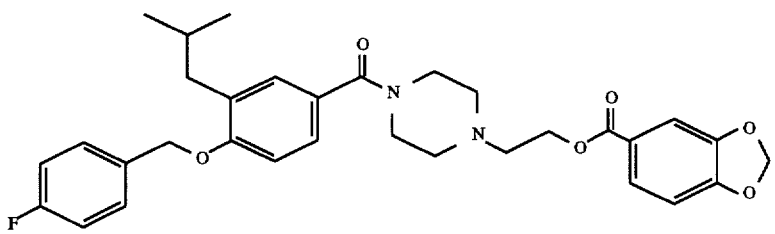

As can be seen from the Examples 1 to 10 in Table 1, the compounds expressed by the above-mentioned formula 1 has an excellent anti-ulcer effect evidenced by the results of the restraint and water immersion stress-induced ulcer inhibition test, while having a high antibacterial activity against *Helicobacter pyrori*. As to $R_1$, while a high anti-ulcer effect is obtained in general when a lower alkyl or, in particular, isobutyl group is used as shown in Examples 1 to 5, 7 and 8; sufficient effects are obtained when an acyl group is introduced in place of the alkyl group as shown in Example 6 or an hydroxy alkyl or its ester is introduced as shown in Examples 9 and 10.

Also, in regard to $R_2$, as compared with $R_1$, a substituent can be selected from a wider range. In particular, as shown in Examples 6, 9, and 10, a lower alkyl group or, in particular, isobutyl group are preferable; while amino group (Example 1), lower alkenyl groups such as isobutenyl group (Example 4), alkoxy groups such as methoxy group (Example 7), nitro group (Example 8), or the like can be selected as well.

TABLE 1

| Example No. | Anti-ulcer Tests | | | | Anti-HP Test | Tests for Safety | | |
|---|---|---|---|---|---|---|---|---|
| | WIS | VOL | TAO | CAP | AHP | PD | AT | MTT |
| 1 | 88 | | | | 25.0–50.0 | | | |
| 2 | 79 | | | 99 | 3.13–6.25 | 2 | | –6 |
| 3 | 69 | | | 85 | | 5 | | –16 |
| 4 | 65 | | | 94 | 25.0 | | 5 | –67 |
| 5 | 59 | | | 96 | 12.5 | | 4 | –84 |
| 6 | 56 | | | 57 | <3.13 | | | –29 |
| 7 | 48 | | | 100 | 25.0–50.0 | | | –72 |
| 8 | 35 | 8 | 16 | 100 | 6.25–12.5 | 2 | | –65 |
| 9 | 88 | | | 100 | | 2 | | 26 |
| 10 | 54 | | | 100 | | | | 34 |

COMPOUND GROUP 2

The N-acylpiperazine derivatives in accordance with this group has a basic structure in which both $R_1$ and $R_2$ are isobutyl group as shown in the following formula 2. These N-acylpiperazine derivatives characteristically have a high anti-ulcer effect in general.

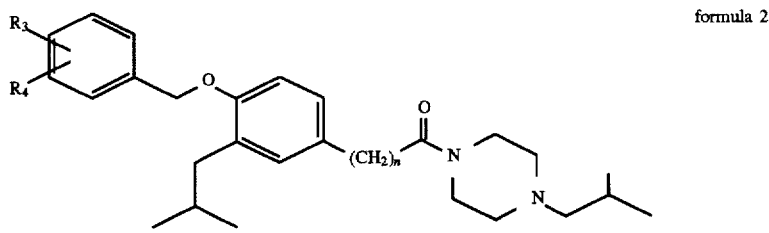

formula 2

The N-acylpiperazine derivatives corresponding to this group include those of the following Examples 11 to 20. The results of their effect tests and safety tests are shown in Table 2.

Example 11

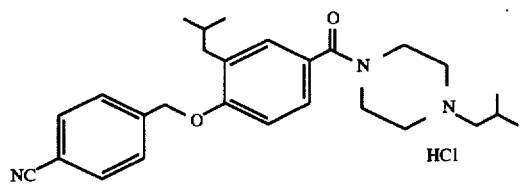

Example 12

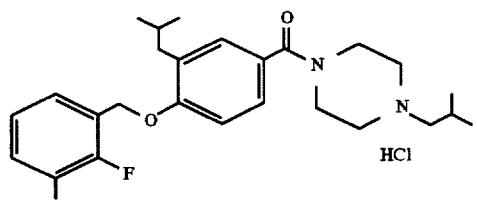

Example 13

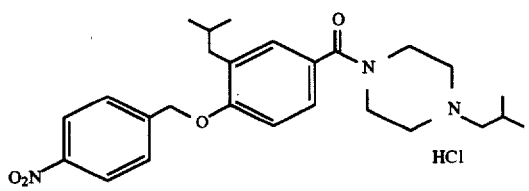

Example 14

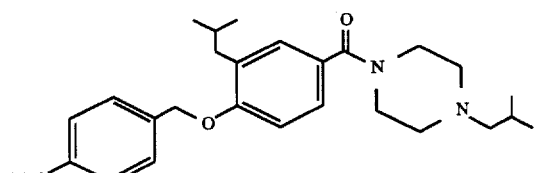

Example 15

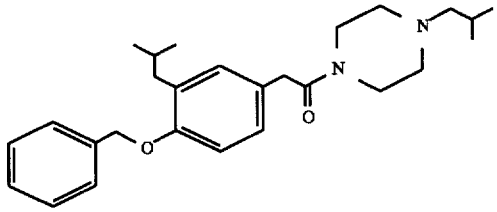

Example 16

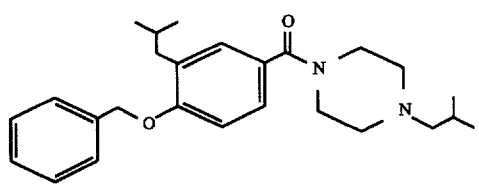

Example 17

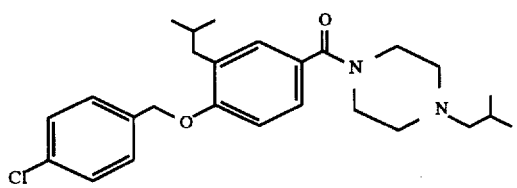

Example 18

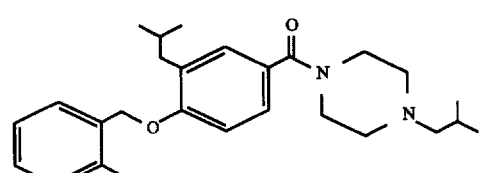

Example 19

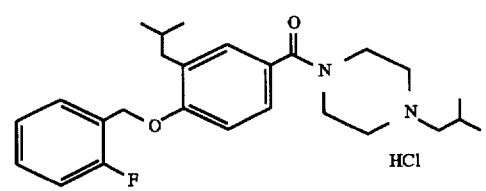

Example 20

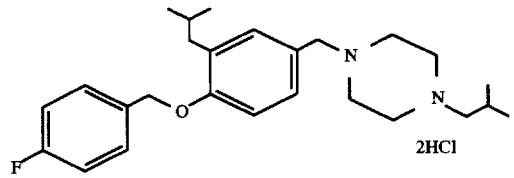

TABLE 2

| Example No. | Anti-ulcer Tests | | | | Anti-HP Test | Tests for Safety | | |
|---|---|---|---|---|---|---|---|---|
| | WIS | VOL | TAO | CAP | AHP | PD | AT | MTT |
| 11 | 94 | | | 100 | | | | −77 |
| 12 | 83 | | | 100 | | 2 | | −15 |
| 13 | 77 | 3 | 18 | | 12.5 | 2 | 5 | −66 |
| 14 | 76 | | | 100 | 25.0 | | | 11 |
| 15 | 71 | | | 99 | | 2 | 2 | −55 |
| 16 | 72 | | | 98 | 50.0 | 5 | 2 | −98 |
| 17 | 66 | | | 99 | 12.5 | 4 | 2 | −18 |
| 18 | 64 | | | 100 | 12.5 | 3 | 4 | −33 |
| 19 | 64 | 6 | 42 | 95 | 12.5–25.0 | 2 | | −55 |
| 20 | 82 | 12 | 43 | 100 | 3.13–6.25 | 2 | | 45 |

As can be seen from the foregoing Examples in Table 2, when $R_1$ and $R_2$ are both isobutyl group, a stably high anti-ulcer effect and a high antibacterial activity against *Helicobacter pyroli* can be obtained. Also, as shown in Example 15, sufficient effects were observed in the case where n is 1. Further, as shown in Example 20, effects were observed when the amide-bond portion was reduced to eliminate oxygen atom of the carbonyl residue.

COMPOUND GROUP 3

The N-acylpiperazine derivatives in accordance with this group has a basic structure in which both $R_1$ and $R_2$ are isobutyl group and $R_3$ is fluorine atom at para-position as shown in the following formula 3.

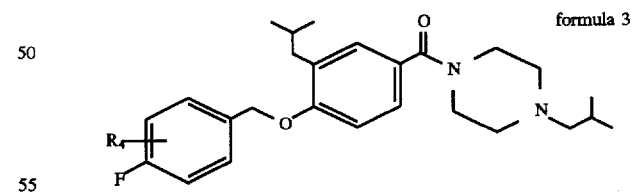

formula 3

These N-acylpiperazine derivatives characteristically have a high anti-ulcer effect and is particularly excellent in safety.

Here, the N-acylpiperazine derivatives corresponding to this group include the following Examples 21 to 27. The results of their effect tests and safety tests are shown in Table 3.

Example 21

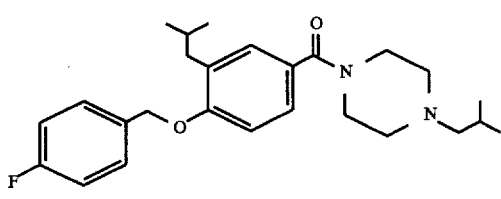

Example 22

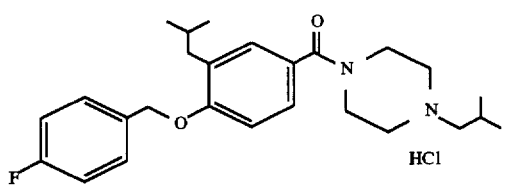
HCl

Example 23

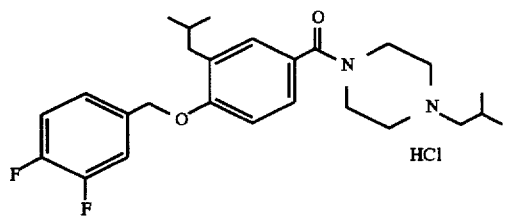
HCl

Example 24

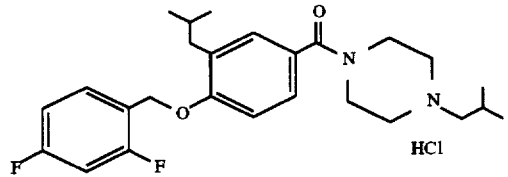
HCl

Example 25

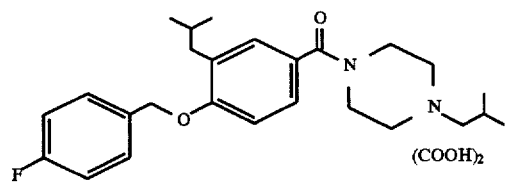
(COOH)₂

Example 26

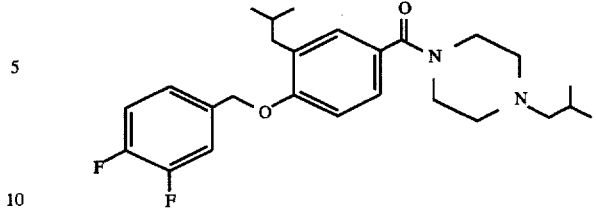

Example 27

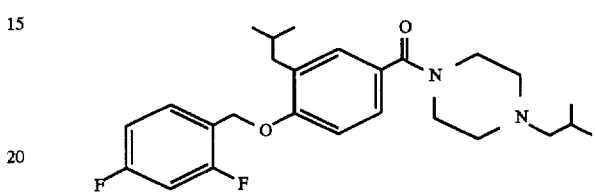

TABLE 3

| Example No. | Anti-ulcer Tests | | | | Anti-HP Test | Tests for Safety | | |
|---|---|---|---|---|---|---|---|---|
| | WIS | VOL | TAO | CAP | AHP | PD | AT | MTT |
| 21 | 84 | 9 | 35 | 100 | 6.25–12.5 | 5 | 5 | –65 |
| 22 | 85 | 10 | 22 | 98 | 12.5 | 5 | 5 | –4 |
| 23 | 83 | –9 | 9 | 99 | 25.0 | | | 28 |
| 24 | 72 | 7 | 33 | 99 | 6.25 | 2 | 4 | –126 |
| 25 | 70 | 19 | 47 | 95 | 12.5 | | | –28 |
| 26 | 63 | | | 99 | 12.5 | | 4 | 29 |
| 27 | 60 | | | 99 | 6.25 | | 5 | –119 |

As can be seen from the foregoing Examples in table 3, when R₃ is fluorine at para-position, an excellent safety can be obtained. For example, when Example 16 in the above-mentioned Compound Group 2 and Example 21 or 22 of this compound Group 3 are compared with each other, due to introduction of fluorine atom at para-position, the acid secretion inhibition effect, anti-ulcer effect, and antibacterial activity against *Helicobacter pyroli* are improved together with a great improvement in safety.

In the following, synthetic methods of intermediates used in Examples explained later will be shown as Reference Examples 1 to 7.

Reference Example 1

Synthesis of ethyl 4-hydroxy-3-methallylbenzoate

Ethyl 4-hydroxybenzoate (50.0 g), methallyl chloride (32.6 g), and potassium carbonate (45.6 g) were refluxed in acetone (150 ml) with stirring for 40 hours. The reaction mixture was filtered and the filtrate was concentrated under a vacuum. The residue, with toluene (150 ml) added thereto, was washed with 2% sodium hydroxide solution and water successively. After being dried over sodium sulfate anhydride, the solution was concentrated under a vacuum. The resulting oily material was dissolved in N,N-dimethylaniline (80 ml) and refluxed with stirring for about 10 hours. The reaction mixture was acidified with concentrated hydrochloric acid while being cooled with ice and then extracted with toluene. The extract was further extracted with 10% aqueous sodium hydroxide solution. The resulting water layer was acidified with concentrated hydrochloric acid and then extracted with toluene. The extract was

23 washed with water, dried over sodium sulfate anhydride, and then concentrated under a vacuum, thereby yielding 59.2 g of the aimed compound.

Reference Example 2
Synthesis of ethyl 4-hydroxy-3-isobutylbenzoate

Ethyl 4-hydroxy-3-methallylbenzoate (25.5 g) was dissolved in ethanol (250 ml) and then, with 10% palladium charcoal (2.6 g) added thereto, this mixture was stirred at room temperature for 41 hours under a hydrogen gas atmosphere. After the reaction mixture was filtered, the filtrate was concentrated under a vacuum, thereby yielding 25.6 g of the aimed oily compound.

Reference Example 3
Synthesis of 4-benzyloxy-3-isobutylbenzoic acid

Ethyl 4-hydroxy-3-isobutylbenzoate (25.6 g), potassium carbonate (31.8 g), and benzyl bromide (23.6 g) were refluxed in acetone (150 ml) with stirring for 4 hours. The reaction mixture, with water added thereto, was extracted with ethyl acetate. The extract was concentrated under a vacuum. The resulting residue, with water (50 ml), potassium hydroxide (12.9 g), and ethanol (100 ml) added thereto, was refluxed with stirring for 2 hours. The reaction mixture, with water added thereto, was neutralized with hydrochloric acid and then extracted with ethyl acetate. The extract was washed with 10% hydrochloric acid and water successively, dried over sodium sulfate anhydride, and then concentrated under a vacuum. Thus obtained solid was recrystallized (from n-hexane/ethanol) so as to yield 29.0 g of the aimed compound.

Reference Example 4
Synthesis of 4-(4-fluorobenzyloxy)-3-isobutylbenzoic acid Ethyl 4-hydroxy-3-isobutylbenzoate (25.6 g), potassium carbonate (31.8 g), and 4-fluorobenzyl bromide (26.1 g) were refluxed in acetone (150 ml) with stirring for 4 hours. The reaction mixture, with water added thereto, was extracted with ethyl acetate. The extract was concentrated under a vacuum. The resulting residue, with water (50 ml), potassium hydroxide (12.9 g), and ethanol (100 ml) added thereto, was refluxed with stirring for 2 hours. The reaction mixture, with water added thereto, was neutralized with hydrochloric acid and then extracted with ethyl acetate. The extract was washed with 10% hydrochloric acid and water successively, dried over sodium sulfate anhydride, and then concentrated under a vacuum. Thus obtained solid was recrystallized (from n-hexane/ethanol), thereby yielding 30.8 g of the aimed compound.

Reference Example 5
Synthesis of 1-isobutylpiperazine dihydrochloride 1-piperazinecarboxaldehyde (33.21 g) was dissolved in acetone (150 ml) and then potassium carbonate (68.34 g) and isobutyl bromide (47.43 g) were added thereto. After being refluxed with stirring for 24 hours, the reaction mixture was filtered. The filtrate was concentrated under a vacuum. The resulting residue was dissolved in ethyl acetate, washed with water and saturated brine successively, dried over sodium suhfate anhydride, and then concentrated under a vacuum. From thus obtained 36.85 g of the residue, 27.8 g were dissolved in methanol (160 ml) and the resulting mixture, with 2N hydrochloric acid methanol solution (180 ml) added thereto, was allowed to stand for 60 hours at room temperature. The mixture was concentrated under a vacuum. To the resulting residue, acetone was added. The resulting crystals were collected filtration, washed with acetone, and then dried to yield 34.8 g of the aimed compound.

24

Reference Example 6
Synthesis of 1-isobutylpiperazine

To 1-isobutylpiperazine dihydrochloride (69.5 g) was added 10% aqueous sodium hydroxide solution (100 ml) and then the resulting mixture was extracted with ether. After the extract was concentrated, the residue was distilled under reduced pressure (bp: 172° to 174° C./5 mmHg), thereby yielding 43.7 g of the aimed compound.

Reference Example 7
Synthesis of 1-isobutyrylpiperazine

Tert-butyl piperazinecarboxylate (2.93 g) and triethylamine (4.39 ml) were dissolved in dichloromethane (60 ml) and then, while being cooled with ice, isobutyryl chloride (1.84 ml) was added thereto. After being stirred for 30 minutes, the reaction mixture was washed with saturated aqueous sodium hydrogencarbonate solution and saturated brine successively, dried over sodium sulfate anhydride, and concentrated under a vacuum. To 1.79 g of part of the resulting residue, trifluoroacetic acid (9 ml) was added and the mixture was stirred for 30 minutes at room temperature. Then, the reaction mixture was concentrated under a vacuum. The residue was dissolved in methanol (20 ml) and then 2N hydrochroric acid methanol solution (10 ml) was added thereto. After being stirred for 10 minutes, the reaction mixture was concentrated under a vacuum. The residue, with 10% aqueous sodium hydroxide solution added thereto, was extracted with chloroform. The extract was washed with water and saturated brine successively, dried over sodium sulfate anhydride, and then concentrated under a vacuum to yield 0.85 g of the aimed compound.

In the following, examples of the compound in accordance with the present invention will be shown.

EXAMPLE 1
1-[3-amino-4-(4-fluorobenzyloxy) benzoyl]-4-isobutylpiperazine dihydrochloride To 85 ml of an ethanol solution containing 1-[4-(4-fluorobenzyloxy)-3-nitrobenzoyl]-4-isobutylpiperazine (HCl free form of Example 8) (17.5g) was added tin (II) chloride monohydrate (47.4 g) and the resulting mixture was stirred at 70° C. for 40 minutes. The mixture was poured into ice water, neutralized with sodium hydrogencarbonate, and then extracted with ethyl acetate. The extract was washed with saturated brine, dried over magnesium sulfate anhydride, and then concentrated under a vacuum. The residue was purified by silica gel column chromatography (ethyl acetate:n-hexane=1:2 to 1:0), thereby yielding 14.5 g of 1-[3-amino-4-(4-fluorobenzyloxy)benzoyl]-4-isobutylpiperazine as a crystal. This compound (1.30 g) was converted into the corresponding hydrochloride salt as in the case of Example 8 which will be explained later, thereby yielding 1.51 g of the aimed compound. This compound is a crystal with a high hygroscopicity.

mp 126.0°–127.3° C.; $^1$H-NMR (DMSO-$d_6$)$\delta$: 7.62(2H, dd, J=8.8,5.4 Hz), 7.32(1H, s), 7.23(2H, t, J=8.8 Hz), 7.19 –7.08(2H, m), 5.22(2H, s), 4.30–2.90(10H, m), 2.94(2H, d, J=6.8 Hz), 2.14–2.04(1H, m), 1.00(6H, d, J=6.4 Hz).

EXAMPLE 2
1-[4-(4-fluorobenzyloxy)benzoyl]-4-isobutylpiperazine hydrochloride As in the case of Example 22 which will be explained later, 1-[4-(4-fluorobenzyloxy)benzoyl]-4-isobutylpiperazine (compound of Example 5) (1.52 g) was converted into the corresponding hydrochloride salt, thereby yielding 1.65 g of the aimed compound.

mp 187.0°–189.0° C.; $^1$H-NMR (CDCl$_3$)$\delta$: 12.94–12.84 (1H, bs), 7.42–7.38(4H, m), 7.09(2H, t, J=8.3 Hz), 6.99(2H, d, J=8.3Hz), 5.06(2H, s), 4.50–3.80(2H, m), 3.64–3.46(2H, m), 2.90–2.60 (6H, m), 2.29–2.19(1H, m), 1.17(6H, d, J=5.4 Hz).

EXAMPLE 3
1-(4-benzyloxybenzoyl)-4-isobutylpiperazine

As in the case of Reference Example 3, ethyl 4-hydroxybenzoate (2.50 g) was benzylated with benzyl bromide (2.57 g) followed by hydrolysis with potassium hydroxide, thereby yielding 3.31 g of 4-benzyloxybenzoic acid as a crystal. In tetrahydrofuran (50 ml), this compound (1.18 g) was suspended together with N,N'-dicyclohexylcarbodiimide (1.14 g) and 4-hydroxybenzotriazole (0.81 g) and then, with 1-isobutylpiperazine (0.71 g) added thereto, stirred at room temperature for 24 hours. The reaction mixture, with water added thereto, was extracted with ethyl acetate. The extract was washed with saturated aqueous sodium hydrogencarbonate solution and saturated brine successively, dried over sodium sulfate anhydride, and then concentrated under a vacuum. The residue was purified by silica gel column chromatography (chloroform:methanol=60:1) and the resulting solid was recrystallized (from n-hexane/ethyl acetate), thereby yielding 1.03 g of the aimed compound.

mp 77.6°–78.4° C.; $^1$H-NMR(CDCl$_3$)δ: 7.43–7.30(7H, m), 6.97(2H, d, J=8.8 Hz), 5.09(2H, s), 2.50–2.25(4H, m), 2.20–2.02(2H, m), 1.85–1.70(1H, m), 0.90(6H, d, J=6.3 Hz).

EXAMPLE 4
1-[4-(4-fluorobenzyloxy)-3-methallylbenzoyl]-4-isobutylpiperazine hydrochloride As in the case of Reference Example 4, ethyl 4-hydroxy-3-methallyl benzoate (1.96 g) was benzylated with 4-fluorobenzyl bromide (1.85 g) followed by hydrolysis, thereby yielding 2.42 g of 4-(4-fluorobenzyloxy)-3-methallylbenzoic acid. As in the case of Example 16, this compound (2.13 g) was subjected to a condensation reaction with 1-isobutylpiperazine (1.01 g), thereby yielding 1-[4(4-fluorobenzyloxy)-3-methallylbenzoyl]-4-isobutylpiperazine. This compound was dissolved in diethyl ether (40 ml) and then 1N hydrogen chloride ether solution (10 ml) was added thereto. The mixture was stirred at room temperature for 10 minutes. The resulting crystals were collected by filtration and recrystallized (from n-hexane/ethanol), thereby yielding 1.88 g of the aimed compound.

mp 163.8°–165.3° C.; $^1$H-NMR (CDCl$_3$)δ: 12.92–12.82 (1H, bs), 7.38(2H, dd, J=8.8,5.4 Hz), 7.34–7.29(2H, m), 7.08(2H, t, J=8.8 Hz), 6.92(1H, d, J=8.3 Hz), 5.07(2H, s),4.82(1H,s), 4.62(1H, s), 4.55–3.75(2H, m), 3.62–3.47(2H, m), 3.37(2H, s), 2.84–2.81(2H,m), 2.86 –2.61(4H, m), 2.29–2.19(1H, m), 1.71(3H, s), 1.16(6H, d, J=6.8 Hz).

EXAMPLE 5
1-[4-(4-fluorobenzyloxy)benzoyl]-4-isobutylpiperazine

It was synthesized in the manner identical to Example 3. Namely, ethyl 4-hydroxybenzoate (2.50 g) was benzylated with 4-fluorobenzyl bromide (2.84 g) and then hydrolyzed. From thus obtained 3.57 g of 4-(4-fluorobenzyloxy) benzoic acid, 1.24 g was subjected to a condensation reaction with 1-isobutylpiperazine (0.71 g), thereby yielding 1.08 g of the aimed compound.

mp 109.0°–110.2° C.; $^1$H-NMR (CDCl$_3$)δ: 7.41(2H, d, J=8.8 Hz), 7.38(2H, d, J=8.8Hz), 7.08(2H, t, J=8.8 Hz), 6.96(2H, d, J=8.8 Hz), 5.05(2H, s), 3.85–3.35(4H, m), 2.50–2.25(4H, m), 2.10(2H, d, J=7.3 Hz), 1.88–1.71(1H, m), 0.90(6H, d, J=6.8 Hz).

EXAMPLE 6
1-[4-(4-fluorobenzyloxy)-3-isobutylbenzoyl]-4-isobutyrylpiperazine

As in the case of Example 16, 4-(4-fluorobenzyloxy)-3-isobutylbenzoic acid (1.51 g) was subjected to a condensation reaction with 1-isobutyrylpiperazine (0.78 g). Thus obtained solid was recrystallized (from ether) to yield 1.98 g of the aimed compound.

mp 86.3°–87.1° C.; $^1$H-NMR (CDCl$_3$)δ: 7.39(2H, dd, J=8.8,5.4 Hz), 7.27(1H, d, J=8.8 Hz), 7.19(1H, s), 7.11(2H, t, J=8.8 Hz), 6.89(1H, d, J=8.8 Hz), 5.06(2H, s), 3.85–3.45 (8H, 2.88–2.75(1H, m), 2.54(2H, d, J=7.3 Hz), 1.98–1.85 (1H, m), 1.15(6H, d, J=6.8 Hz), 0.90(6H, d, J=6.8 Hz).

EXAMPLE 7
1-[4-(4-fluorobenzyloxy)-3-methoxybenzoyl]-4-isobutylpiperazine hydrochloride In a manner identical to Reference Example 4, ethyl 4-hydroxy-3-methoxybenzoate (4.10 g) was benzylated with 4-fluorobenzyl bromide (4.35 g) and then hydrolyzed to yield 5.57 g of 4-(4-fluorobenzyloxy)-3-methoxybenzoic acid. In a manner similar to Example 8, this material (1.38 g) were subjected to a condensation reaction with 1-isobutylpiperazine dihydrochloride (1.08 g), thereby yielding 2.24 g of 1-[4-(4-fluorobenzyloxy)-3-methoxybenzoyl]-4-isobutyl piperazine. This material was dissolved in diethyl ether (50 ml) and then 1N hydrogen chloride ether solution (10 ml) was added thereto. The mixture was stirred at room temperature for 10 minutes and then the resulting crystals were collected by filtration and recrystallized (from n-hexane/ethanol), thereby yielding 1.60 g of the aimed compound.

mp 197.7°–200.4° C.; $^1$H-NMR (CDCl$_3$)δ: 12.85–12.75 (1H, bs), 7.41(2H, dd, J=8.8,5.4 Hz), 7.06(2H, t, J=8.8 Hz), 7.01(1H, s), 6.96(1H, d, J=8.3 Hz), 6.88(1H, d, J=8.3 Hz), 5.13(2H, s), 4.80–3.95(4H, m), 3.89(3H, s), 3.62–3.47(2H, m), 2.90–2.78(2H, m), 2.90–2.65(2H, m), 2.29–2.19(1H, m), 1.16(6H, d, J=6.8 Hz).

EXAMPLE 8
1-[4-(4-fluorobenzyloxy)-3-nitrobenzoyl]-4-isobutylpiperazine hydrochloride To 500 ml of ethanol containing 4-hydroxy-3-nitrobenzoic acid (50.0 g) was added concentrated sulfturic acid (33.0 ml) and the resulting mixture was refluxed with stirring for 20 hours. After this reaction mixture was concentrated under a vacuum, the residue was diluted with water and then the crystal was collected by filtration. This crystal was suspended in water and neutralized in saturated aqueous sodium hydrogencarbonate solution. Thereafter, the crystal was collected by filtration, washed with water, and dried under a vacuum, thereby yielding 54.0 g of ethyl 4-hydroxy-3-nitrobenzoate. As in the case of Reference Example 4, this compound (46.6 g) was benzylated with 4-fluorobenzyl bromide (50.0 g) folowed by hydrolysis with potassium hydroxide, thereby yielding 58.0 g of 4-(4-fluorobenzyloxy)-3-nitrobenzoic acid. To 180 ml of a chloroform solution containing this compound (16.0 g), triethylamine (15.3 ml) and diphenylphosphinic chloride (10.5 ml) were added. After the resulting mixture was stirred for 1 hour, 1-isobutylpiperazine dihydrochloride (11.8 g) and triethylamine (15.3 ml) were added and the mixture was stirred for 13 hours at room temperature. The reaction mixture was successively washed with water, saturated aqueous sodium hydrogencarbonate solution, and saturated brine, dried over magnesium sulfate anhydride, and then concentrated under a vacuum. The residue was purified by silica gel column chromatography (ethyl acetate:n-hexane=1:2 to 1:1), thereby yielding 19.8 g of 1-[4-(4-fluorobenzyloxy)-3-nitrobenzoyl]-4-isobutylpiperazine as a crystal. To 20 ml of ethyl acetate solution containing this compound (1.38 g), 1N hydrogen chloride ether solution (3.4 ml) was added. After the mixture was stirred for 15 minutes at room temperature, the resulting crystals were collected by filtration, thereby yielding 1.48 g of the aimed compound.

m.p. 184.5°–185.8° C.; $^1$H-NMR (CDCl$_3$)δ: 12.99–12.90 (1H, bs), 8.00(1H, s), 7.62(1H, d, J=8.8 Hz), 7.44(2H, dd, J=8.8,5.4 Hz), 7.18(1H, d, J=8.8 Hz), 7.09(2H, t, J=8.8 Hz), 5.24(2H, s), 4.55–3.95(4H, m), 3.62–3.40(2H, m), 2.85(4H, s), 2.29–2.19(1H, m), 1.17(6H, d, J=6.4 Hz).

EXAMPLE 9

1-[4-(4-fluorobenzyloxy)-3-isobutylbenzoyl]-4-(2-hydroxyethyl)piperazine 4-(4-fluorobenzyloxy)-3-isobutylbenzoic acid (2.72 g) was dissolved in a mixture of chloroform (50 ml) and triethylamine (2.50 ml). To the mixture, diphenylphosphinic chloride (1.72 ml) was added while being cooled with ice. After being stirred for 40 minutes, the mixture, with 1-(2-hydroxyethyl)piperazine (1.11 ml) added thereto, was stirred for 1.5 hours at room temperature. The reaction mixture was washed with saturated aqueous sodium hydrogencarbonate solution and saturated brine successively, dried over sodium sulfate anhydride, and then concentrated under a vacuum. The residue was purified by silica gel column chromatography (chloroform:methanol=30:1) and the resulting solid was recrystallized (from diethyl ether), thereby yielding 3.50 g of the aimed compound.

mp 83.5°–85.0° C.; $^1$H-NMR (CDCl$_3$)δ: 7.39(2H, dd, J=8.8,5.4 Hz), 7.24(1H, d, J=8.8 Hz), 7.18(1H, s), 7.08(2H, t, J=8.8 Hz), 6.88(1H, d, J=8.8 Hz), 5.05(2H, s), 3.90–3.40 (1H, bs), 3.65(4H, t, J=5.4 Hz), 2.63–2.46(10H, m), 2.01–1.91(1H, m), 0.90(6H, d, J=6.8 Hz).

EXAMPLE 10

1-[4-(4-fluorobenzyloxy)-3-isobutylbenzoyl]-4-[2-(piperonyloyloxy)ethyl]piperazine 1-[4-(4-fluorobenzyloxy)-3-isobutylbenzoyl]-4-(2-hydroxyethyl) piperazine (1.95 g) was dissolved in a mixture of dichloromethane (30 ml) and triethylamine (1.04 ml) and then, while being cooled with ice, piperonyloyl chloride (0.93 g) was added thereto dropwise. After being stirred for 12 hours at room temperature, the reaction mixture was washed with saturated aqueous sodium hydrogencarbonate solution and saturated brine successively, dried over sodium sulfate anhydride, and then concentrated under a vacuum. Thus obtained residue was purified by silica gel column chromatography (chloroform:methanol=50:1), thereby yielding 1.92 g of the aimed compound.

$^1$H-NMR (CDCl$_3$)δ: 7.63(1H, d, J=8.8 Hz), 7.45(1H, s), 7.39(2H, dd, J=8.8,5.4 Hz), 7.25(1H, d, J=8.8 Hz), 7.17(1H, s), 7.08(2H, t, J=8.8 Hz), 6.87(1H, d, J=8.8 Hz), 6.84(1H, d, J=8.8 Hz), 6.04(2H, s), 5.05(2H, s), 4.42(2H, t, J=5.8 Hz), 3.88–3.38(4H, m), 2.79 (2H, t, J=5.8 Hz), 2.68–2.46(4H, m), 2.53(2H, d, J=6.8 Hz), 1.98–1.85(1H, m), 0.89(6H, d, J=6.8 Hz).

EXAMPLE 11

1-[4-(4-cyanobenzyloxy)-3-isobutylbenzoyl]-4-isobutylpiperazine hydrochloride

As in the case of Example 18, 1-(4-hydroxy-3-isobutylbenzoyl)-4-isobutylpiperazine (intermediate of Example 18) (1.50 g) was benzylated with 4-cyanobenzyl bromide (1.02 g), thereby yielding 1-[4-(4-cyanobenzyloxy)-3-isobutylbenzoyl]-4-isobutylpiperazine. This compound was converted into the corresponding hydrochloride salt as in the case of Example 22, thereby yielding 2.05 g of the aimed compound.

mp 159.2°–161.5° C.; $^1$H-NMR (CDCl$_3$)δ: 12.90–12.80 (1H, bs), 7.71(2H, d, J=8.3 Hz), 7.54(2H, d, J=8.3 Hz), 7.31–7.23(2H, m), 6.86(1H, d, J=8.3 Hz), 5.17(2H, s), 4.85–3.80(2H, m), 3.65–3.45(2H, m), 2.95–2.60(6H, m), 2.56(2H, d, J=6.8 Hz), 2.29–2.19(1H, m), 1.98–1.88(1H, m), 1.17(6H, d, J=6.4 Hz), 0.91(6H, d, J=6.4 Hz).

EXAMPLE 12

1-[4-(2-fluoro-3-methylbenzyloxy)-3-isobutylbenzoyl]-4-isobutylpiperazine hydrochloride As in the case of Example 18, 1-(4-hydroxy-3-isobutylbenzoyl)-4-isobutylpiperazine (1.59 g) was benzylated with 2-fluoro-3-methylbenzyl bromide (1.12 g), thereby yielding 1-[4-(2-fluoro-3-methylbenzyloxy)-3-isobutylbenzoyl]-4-isobutylpiperazine. This compound was converted into the corresponding hydrochloride salt as in the case of Example 22, thereby yielding 2.05 g of the aimed compound.

mp 144.1°–147.6° C.; $^1$H-NMR (CDCl$_3$)δ: 12.82–12.72 (1H, bs), 7.32–7.29(2H, m), 7.28–7.16(2H, m), 7.06(1H, t, J=7.8Hz), 6.95(1H, d, J=8.3Hz), 5.15(2H, s), 4.80–3.80(2H, m), 3.62–3.42(2H, m), 2.85–2.82(2H, m), 2.84–2.62(4H, m), 2.54(2H, d, J=6.8 Hz), 2.31(3H, s), 2.29–2.19(1H, m), 1.98–1.88(1H, m), 1.16(6H, d, J=6.4 Hz), 0.89(6H, d, J=6.8 Hz).

EXAMPLE 13

1-isobutyl-4-[3-isobutyl-4-(4-nitrobenzyloxy)benzoyl]piperazine hydrochloride

As in the case of Example 18, 1-(4-hydroxy-3-isobutylbenzoyl)-4-isobutylpiperazine (1.59 g) was benzylated with 4-nitrobenzyl bromide (1.19 g), thereby yielding 1-isobutyl-4-[3-isobutyl-4-(4-nitrobenzyloxy)benzoyl] piperazine. This compound was dissolved in a mixture of diethyl ether and tetrahydrofuran and then 1N hydrogen chloride ether solution (7 ml) was added. After being stirred for 10 minutes at room temperature, the resulting crystals were collected by filtration and then recrystallized (from n-hexane/ethanol), thereby yielding 1.22 g of the aimed compound.

mp 159.6°–161.3° C.; $^1$H-NMR (CDCl$_3$)δ: 12.96–12.86 (1H, bs), 8.28(2H, d, J=8.8 Hz), 7.60(2H, d, J=8.8 Hz), 7.31–7.25(2H, m), 6.87(1H, d, J=8.8 Hz), 5.22(2H, s), 4.50–3.80(2H, m), 3.64–3.46(2H, m), 2.84–2.81(2H, m), 2.90–2.60(4H, m), 2.58(2H, d, J=6.8 Hz), 2.29–2.19(1H, m), 1.98–1.88(1H, m ), 1.17(6H, d, J=6.4 Hz), 0.92(6H, d, J=6.4 Hz).

EXAMPLE 14

1-isobutyl-4-[3-isobutyl-4-(4-methoxybenzyloxy)benzoyl] piperazine

As in the case of Example 18, 1-(4-hydroxy-3-isobutylbenzoyl)-4-isobutylpiperazine (1.59 g) was benzylated with 4-methoxybenzyl bromide (0.94 g), thereby yielding 1.69 g of the aimed compound.

$^1$H-NMR (CDCl$_3$)δ: 7.34(2H, d, J=8.8 Hz), 7.25(1H, d, J=8.8 Hz), 7.16(1H, s), 6.92(2H, d, J=8.8 Hz), 6.89(1H, d, J=8.8 Hz), 5.01(2H, s), 3.82(3H, s), 3.85–3.35(4H, m), 2.52 (2H, d, J=6.8 Hz), 2.55–2.25(4H, m), 2.10(2H, d, J=7.3 Hz), 2.01–1.91(1H, m), 1.88–1.71(1H, m), 0.90(6H, d, J=6.8 Hz), 0.89(6H, d, J=6.4 Hz).

EXAMPLE 15

1-(4-benzyloxy-3-isobutylphenylacetyl)-4-isobutylpiperazine

A mixed solution comprising 4-hydroxyphenylacetic acid (150.0 g), toluene (250 ml), ethanol (150 ml), and p-toluenesulfonic acid (50 g) was refluxed with stirring for 3 hours. The reaction mixture was washed with aqueous sodium hydrogencarbonate solution, dried over sodium sulfate anhydride, and then concentrated under a vacuum to yield 164.3 g of oily ethyl 4-hydroxyphenylacetate. This material was subjected to a reaction identical to that of Reference Example 1, thereby yielding 138.2 g of oily ethyl 4-hydroxy-3-methallylphenylacetate. In a manner identical to Reference Examples 2 and 3, this material was successively subjected to catalytic reduction, benzylation, and hydrolysis reactions, thereby yielding 70.4 g of 4-benzyloxy-3-isobutylphenylacetic acid. As in the case of Example 3, this material (1.0 g) was subjected to a condensation reaction with 1-isobutylpiperazine (0.48 g), thereby yielding 1.3 g of the aimed compound.

$^1$H-NMR (CDCl$_3$)δ: 7.44–7.29(5H, m), 7.01–6.98(2H, m), 6.83(1H, d, J=8.3 Hz), 5.05(2H, s), 3.64(4H, s), 3.52–3.38(2H, m), 2.52(2H, d, J=6.8 Hz), 2.43–2.27(2H, m), 2.25–2.10(2H, m), 2.09–2.02(2H, m), 2.01–1.91(1H, m), 1.88–1.71(1H, m), 0.89(12H, d, J=6.8 Hz).

EXAMPLE 16
1-(4-benzyloxy-3-isobutylbenzoyl)-4-isobutylpiperazine 4-benzyloxy-3-isobutylbenzoic acid (4.94 g) was dissolved in a mixture of chloroform (60 ml) and triethylamine (4.83 ml). To this mixture, diphenylphosphinic chloride (3.66 ml) was added while being cooled with ice. After being stirred for 40 minutes, the mixture, with 1-isobutylpiperazine (2.48 g) added thereto, was stirred for 1.5 hours at room temperature. The reaction mixture was washed with saturated aqueous sodium hydrogencarbonate solution and saturated brine successively, dried over sodium sulfate anhydride, and then concentrated under a vacuum. Thus obtained residue was purified by silica gel column chromatography (chloroform: methanol=50:1), thereby yielding 7.11 g of the aimed compound.

$^1$H-NMR (CDCl$_3$)δ: 7.44–7.37(4H, m), 7.33(1H, d, J=8.8 Hz), 7.26–7.23(1H, m), 7.17(1H, s), 6.89(1H, d, J=8.8 Hz), 5.10(2H, s), 3.90–3.35(4H, m), 2.55(2H, d, J=7.3 Hz), 2.55–2.25(4H, m), 2.10(2H, d, J=7.3 Hz), 2.01–1.91(1H, m), 1.88–1.71(1H, m), 0.91(6H, d, J=6.8 Hz), 0.90(6H, d, J=6.8 Hz).

EXAMPLE 17
1-[4-(4-chlorobenzyloxy)-3-isobutylbenzoyl]-4-isobutylpiperazine

As in the case of Example 18, 1-(4-hydroxy-3-isobutylbenzoyl)-4-isobutylpiperazine (1.59 g) was benzylated with 4-chlorobenzyl bromide (1.03 g), thereby yielding 0.95 g of the aimed compound.

$^1$H-NMR (CDCl$_3$)δ: 7.38–7.34(4H, m), 7.24(1H, d, J=8.3 Hz), 7.17(1H, s), 6.85(1H, d, J=8.3 Hz), 5.05(2H, s), 3.80–3.30(4H, m), 2.54(2H, d, J=7.3 Hz), 2.55–2.25(4H, m), 2.10(2H, d, J=7.3 Hz), 2.01–1.91(1H, m), 1.88–1.71(1H, m), 0.90(12H, d, J=6.8 Hz).

EXAMPLE 18
1-[4-(2-fluorobenzyloxy)-3-isobutylbenzoyl]-4-isobutylpiperazine 1-(4-benzyloxy-3-isobutylbenzoyl)-4-isobutylpiperazine (6.78 g) was dissolved in ethanol (250 ml) and then, with 10% palladium charcoal (0.14 g) added thereto, the mixture was stirred at room temperature for 24 hours in a hydrogen gas atmosphere. After the reaction mixture was filtered under a suction, the filtrate was concentrated under a vacuum, thereby yielding 4.73 g of 1-(4-hydroxy-3-isobutylbenzoyl)-4-isobutylpiperazine. In acetone (50 ml), this compound (0.96 g), 2-fluorobenzyl bromide (0.68 g), and potassium carbonate (0.83 g) of were refluxed with stirring for 4 hours. The reaction mixture, with water added thereto, was extracted with ethyl acetate. The extract was washed with saturated aqueous sodium hydrogencarbonate solution and saturated brine successively, and then dried over sodium sulfate anhydride. The residue obtained after concentration was purified by silica gel column chromatography (ethyl acetate:n-hexane=1:2), thereby yielding 0.90 g of the aimed compound.

$^1$H-NMR (CDCl$_3$)δ: 7.50(1H, t, J=8.8 Hz), 7.37–7.15(4H, m), 7.09(1H, t, J=8.8 Hz), 6.92(1H, d, J=8.8 Hz), 5.16(2H, s), 3.80–3.30(4H, m), 2.54 (2H, d, J=7.3 Hz), 2.55–2.25(4H, m), 2.10(2H, d, J=7.3 Hz), 2.01–1.91(1H, m), 1.88–1.71(1H, m), 0.90(12H, d, J=7.3 Hz).

EXAMPLE 19
1-[4-(2-fluorobenzyloxy)-3-isobutylbenzoyl]-4-isobutylpiperazine hydrochloride As in the case of Example 22, 1-[4-(2-fluorobenzyloxy)-3-isobutylbenzoyl]-4-isobutylpiperazine (1.04 g) was converted into the corresponding hydrochloride salt and then recrystallized (from n-hexane/ethanol), thereby yielding 1.29 g of the aimed compound.

mp 170.0°–171.5° C.; $^1$H-NMR (CDCl$_3$)δ: 12.96–12.86 (1H, bs), 7.48(1H, t, J=8.3 Hz), 7.31–7.08(5H, m), 6.95(1H, d, J=8.3 Hz), 5.17(2H, s), 4.50–3.70(2H, m), 3.64–3.46(2H, m), 2.89–2.78(2H, m), 2.82–2.60(4H, m), 2.54(2H, d, J=6.8 Hz), 2.29–2.19(1H, m), 1.98–1.88(1H, m), 1.17(6H, d, J=6.4 Hz), 0.89(6H, d, J=6.4 Hz).

EXAMPLE 20
b 1-[4-(4-fluorobenzyloxy)-3-isobutylbenzyl]-4-isobutylpiperazine dihydrochloride To a suspension of lithium aluminum hydride (0.28 g) in tetrahydrofuran (50 ml), 15 ml of a tetrahydrofuran solution containing 1-[4-(4-fluorobenzyloxy)-3-isobutylbenzoyl]-4-isobutylpiperazine (compound of Example 21) (2.13 g) were added. After this mixture was refluxed with stirring for 4 hours, water was added thereto to decompose the excess reagent and then the mixture was filtered. The filtrate was extracted with ethyl acetate. The extract was washed with saturated aqueous sodium hydrogencarbonate solution and saturated brine successively, dried over sodium sulfate anhydride, and concentrated under a vacuum. As in the case of Example 22, the residue was converted into the corresponding hydrochloride salt, thereby yielding 1.79 g of the aimed compound.

mp 236.7°–239.3° C.; $^1$H-NMR(CDCl$_3$)δ: 7.47–7.36(4H, m), 7.19(2H,t,J=8.3 Hz), 7.05(1H,d,J=8.3 Hz), 5.07(2H,s), 3.85–3.35(4H,m), 2.54–2.40(4H,m), 2.45(2H,s), 2.42(2H,d, J=6.8 Hz), 2.01–1.91(1H,m), 1.88–1.71(1H,m), 0.94(6H,dj= 6.4 Hz), 0.81(6H,d,J=6.4 Hz).

EXAMPLE 21
1-[4-(4-fluorobenzyloxy)-3-isobutylbenzoyl]-4-isobutylpiperazine 4-(4-fluorobenzyloxy)-3-isobutylbenzoic acid (16.5 g) was dissolved in a mixture of chloroform (150 ml) and triethylamine (15.3 ml). To this mixture was added diphenylphosphinic chloride (11.5 ml) while being cooled with ice. After being stirred for 40 minutes, the mixture, with 1-isobutylpiperazine (7.83 g) added thereto, was stirred for 1.5 hours at room temperature. This reaction mixture was washed with saturated sodium hydrogencarbonate solution and saturated brine successively, dried over sodium sulfate anhydride, and then concentrated under a vacuum. Thus obtained residue was purified by silica gel column chromatography (chloroform: methanol=50:1) and the resulting solid was recrystallized (from n-hexane), thereby yielding 19.6 g of the aimed compound.

mp 77.0°–78.0° C.; $^1$H-NMR (CDCl$_3$)δ: 7.39(2H, dd, J=8.8,5.4 Hz), 7.25(1H, d, J=8.8 Hz), 7.17(1H, s), 7.08(2H, t, J=8.8 Hz), 6.87(1H, d, J=8.8 Hz), 5.05(2H, s), 3.90–3.35 (4H, m), 2.53(2H, d, J=6.8 Hz), 2.55–2.25(4H, m), 2.10(2H, d, J=7.3 Hz), 2.01–1.91(1H, m), 1.88–1.71(1H, m), 0.90(6H, d, J=6.4 Hz), 0.89(6H, d, J=6.8 Hz).

EXAMPLE 22

1-[4-(4-fluorobenzyloxy)-3-isobutylbenzoyl]-4-isobutylpiperazine hydrochloride

1-[4-(4-fluorobenzyloxy)-3-isobutylbenzoyl]-4-isobutylpiperazine (3.18 g) was dissolved in diethyl ether (20 ml) and then 15 ml of 1N hydrogen chloride in ether was added. After this mixture was stirred for 10 minutes at room temperature, the resulting crystals were collected by filtration, thereby yielding 4.40 g of the aimed compound.

mp 166.7°–168.7° C.; $^1$H-NMR (CDCl$_3$)δ: 12.95–12.85 (1H, bs), 7.39(2H, dd, J=8.3,5.4 Hz), 7.31–7.28(1H, m), 7.21(1H, s), 7.09(2H, t, J=8.3 Hz), 6.90(1H, d, J=8.3 Hz), 5.07(2H, s), 4.60–3.90(2H, m), 3.64–3.46(2H, m), 2.84–2.81(2H, m), 2.85–2.60(4H, m), 2.53(2H, d, J=7.3 Hz), 2.29–2.19(1H, m), 1.98–1.88(1H, m), 1.17(6H, d, J=6.8 Hz), 0.89(6H, d, J=6.8 Hz).

EXAMPLE 23

1-[4-(3,4-difluorobenzyloxy)-3-isobutylbenzoyl]-4-isobutylpiperazine hydrochloride As in the case of Example 22, 1-[4-(3,4-difluorobenzyloxy)-3-isobutylbenzoyl]-4-isobutylpiperazine (compound of Example 26) (2.24 g) was converted into the c or respon ding hydrochloride salt, thereby yielding 2.03 g of the aimed compound.

mp 161.5°–163.5° C.; $^1$H-NMR (CDCl$_3$)δ: 12.89–12.79 (1H, bs), 7.31–7.14(5H, m), 6.87(1H, d, J=8.8 Hz), 5.05(2H, s), 4.50–3.80(2H, m), 3.64–3.46(2H, m), 2.84–2.81(2H, m), 2.90–2.60(4H, m), 2.54(2H, d, J=7.3 Hz), 2.29–2.19(1H, m), 1.98–1.88(1H, m), 1.17(6H, d, J=6.8 Hz), 0.91(6H, d, J=6.8 Hz).

EXAMPLE 24

1-[4-(2,4-difluorobenzyloxy)-3-isobutylbenzoyl]-4-isobutylpiperazine hydrochloride As in the case of Example 22, 1-[4-(2,4-difluorobenzyloxy)-3-isobutylbenzoyl]-4-isobutylpiperazine (compound of Example 27) (0.49 g) was converted into the corresponding hydrochloride salt, thereby yielding 0.52 g of the aimed compound.

mp 152.2°–154.8° C.; $^1$H-NMR (CDCl$_3$)δ: 12.97–12.87 (1H, bs), 7.48–7.42(1H, m), 7.32–7.30(1H, m), 7.21(1H, s), 6.94(1H, d, J=8.3 Hz), 6.90–6.84(2H, m), 5.11(2H, s), 4.30–3.80(2H, m), 3.60–3.45(2H, m), 2.90–2.60(4H, m), 2.84–2.81(2H, m), 2.51(2H, d, J=7.3 Hz), 2.30–2.20(1H, m), 1.96–1.87(1H, m), 1.00(6H, d, J=6.8 Hz), 0.83(6H, d, J=6.4 Hz).

EXAMPLE 25

1-[4-(4-fluorobenzyloxy)-3-isobutylbenzoyl]-4-isobutylpiperazine oxalate

1-[4-(4-fluorobenzyloxy)-3-isobutylbenzoyl]-4-isobutylpiperazine (1.01 g) was dissolved in diethyl ether (10 ml) and then 10 ml of a diethyl ether solution containing oxalic acid (0.4 g) was added thereto. After this mixture was stirred for 10 minutes at room temperature, the resulting crystals were collected by filtration and then recrystallized (from n-hexane/ethanol), thereby yielding 0.93 g of the aimed compound.

mp 168.0°–169.4° C.; $^1$H-NMR (CDCl$_3$)δ: 7.39(2H, dd, J=8.3,5.4 Hz), 7.32–7.28(1H, m), 7.20(1H, s), 7.09(2H, t, J=8.3 Hz), 6.90(1H, d, J=8.3 Hz), 5.07(2H, s), 4.20–3.80 (4H, m), 3.30–3.00(2H, m), 2.90(2H, d, J=6.8 Hz), 2.53(2H, d, J=6.8 Hz), 2.80–2.20(4H, m), 2.18–2.05(1H, m), 1.98–1.85(1H, m), 1.04(6H, d, J=6.8 Hz), 0.89(6H, d, J=6.8 Hz).

EXAMPLE 26

1-[4-(3,4-difluorobenzyloxy)-3-isobutylbenzoyl]-4-isobutylpiperazine

As in the case of Example 18, 1-(4-hydroxy-3-isobutylbenzoyl)-4-isobutylpiperazine (1.24 g) was benzylated with 3,4-difluorobenzyl bromide (1.60 g), thereby yielding 1.67 g of the aimed compound.

$^1$H-NMR (CDCl$_3$)δ: 7.28–7.11(5H, m), 6.84(1H, d, J=8.3 Hz), 5.03(2H, s), 3.85–3.35(4H, m), 2.54 (2H, d, J=7.3 Hz), 2.55–2.25(4H, m), 2.10(2H, d, J=7.3 Hz), 2.01–1.91(1H, m), 1.88–1.71(1H, m), 0.91(6H, d, J=6.8 Hz), 0.90(6H, d, J=6.4 Hz).

EXAMPLE 27

1-[4-(2,4-difluorobenzyloxy)-3-isobutylbenzoyl]-4-isobutylpiperazine

As in the case of Example 18, 1-(4-hydroxy-3-isobutylbenzoyl)-4-isobutylpiperazine (1.60 g) was benzylated with 2,4-difluorobenzyl bromide (1.24 g), thereby yielding 1.67 g of the aimed compound.

$^1$H-NMR (CDCl$_3$)δ: 7.49–7.42(1H, m), 7.26(1H, d, J=8.3 Hz), 7.18(1H, s), 6.94–6.82(3H, m), 5.10(2H, s), 3.85–3.35 (4H, m), 2.52 (2H, d, J=7.3 Hz), 2.48–2.30(4H, m), 2.10(2H, d, J=7.3 Hz), 2.01–1.91(1H, m), 1.88–1.71(1H, m), 0.90(6H, d, J=6.4 Hz), 0.89(6H, d, J=6.8 Hz).

What is claimed is:

1. An N-acylpiperazine compound or a pharmacologically acceptable salt thereof expressed by the following formula 1:

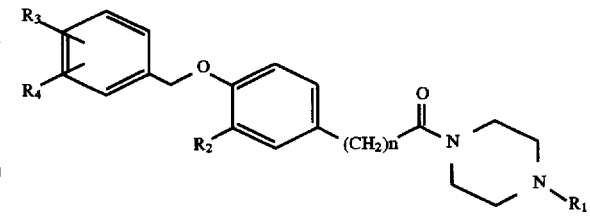

wherein $R_1$ represents a branched lower alkyl, hydroxy lower alkyl, lower acyl, phenylcarbonyloxy lower alkyl, or 3,4-methylenedioxyphenylcarbonyloxy lower alkyl group;

$R_2$ represents hydrogen, a lower alkyl, lower alkoxy, lower alkenyl, amino, or nitro group;

$R_3$ and $R_4$, which are identical to or different from each other, represent hydrogen, halogen, cyano, nitro, a lower alkyl, or lower alkoxy group, wherein said $R_3$ and R can not be hydrogen at the same time; and n represents 0 or 1.

2. An N-acylpiperazine compound or a pharmacologically acceptable salt thereof according to claim 1, wherein $R_2$ is a branched lower alkyl group.

3. An N-acylpiperazine compound or a pharmacologically acceptable salt thereof according to claim 1, wherein each of $R_1$ and $R_2$ is a branched lower alkyl group.

4. An N-acylpiperazine compound or a pharmacologically acceptable salt thereof according to claim 1, wherein at least one of $R_1$ and $R_2$ is isobutyl.

5. An N-acylpiperazine compound or a pharmacologically acceptable salt thereof according to claim 1, wherein at least one of $R_3$ and $R_4$ is fluorine.

6. An N-acylpiperazine compound or a pharmacologically acceptable salt thereof according to claim 5, wherein said fluorine atom is bonded to para-position.

7. An N-acylpiperazine compound or a pharmacologically acceptable salt thereof according to claim 1, wherein each of $R_1$ and $R_2$ is isobutyl, while $R_3$ is fluorine atom bonded to para-position.

8. An N-acylpiperazine compound or a pharmacologically acceptable salt according to claim 1, wherein $R_2$ represents a lower alkyl, lower alkoxy, lower alkenyl, amino, or nitro.

9. An anti-ulcer drug or an antibacterial drug against *Helicobacter pyroli* comprising, as an effective ingredient, an N-acylpiperazine compound or a pharmacologically acceptable salt thereof according to claim 1, together with a pharmacologically acceptable carrier and/or adjuvant.

10. An anti-ulcer drug according to claim 9, wherein said pharmacologically acceptable salt is hydrochloride or oxalate.

11. A method for treating peptic ulcers in mammals comprising: administering to a host of a therapeutically effective amount of an N-acylpiperazine compound or a pharmacologically acceptable salt thereof having a formula:

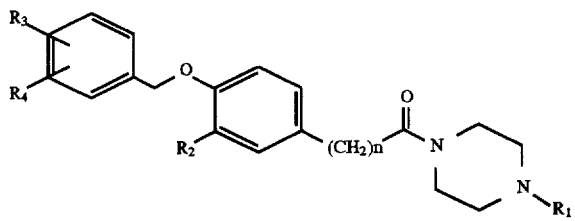

wherein $R_1$ represents a lower alkyl, hydroxy lower alkyl, lower acyl, phenylcarbonyloxy lower alkyl, or 3,4-methylenedioxyphenylcarbonyloxy lower alkyl group;

$R_2$ represents hydrogen, lower alkyl, lower alkoxy, lower alkenyl, amino, or nitro;

$R_3$ and $R_4$, which are identical to or different from each other, represent hydrogen, halogen, cyano, nitro, lower alkyl, or lower alkoxy group; and n represents 0 or 1.

12. A method according to claim 11, wherein said peptic ulcers are gastric ulcers in man.

13. A method for inhibiting acid secretion in stomach of mammals comprising: administering to a host of an effective amount of an N-acylpiperazine compound or a pharmacologically acceptable salt thereof having a formula:

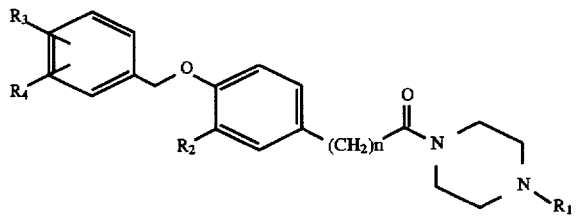

wherein $R_1$ represents lower alkyl, hydroxy lower alkyl, lower acyl, phenylcarbonyloxy lower alkyl, or 3,4-methylenedioxyphenylcarbonyloxy lower alkyl group;

$R_2$ represents hydrogen, lower alkyl, lower alkoxy, lower alkenyl, amino, or nitro;

$R_3$ and $R_4$, which are identical to or different from each other, represent hydrogen, halogen, cyano, nitro, lower alkyl, or lower alkoxy group; and n represents 0 or 1.

14. A method for inhibiting growth of *Helicobacter pyroli* in stomach of mammals, which comprises administering to a host of an effective amount of an N-acylpiperazine compound or a pharmacologically acceptable salt thereof having a formula:

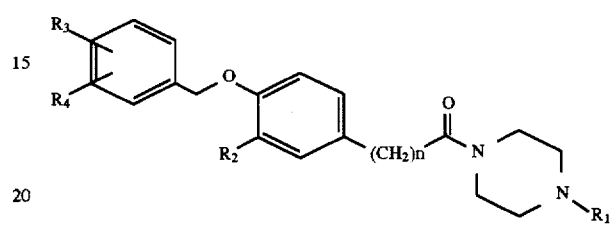

wherein $R_1$ represents a lower alkyl, hydroxy lower alkyl, lower acyl, phenylcarbonyloxy lower alkyl, or 3,4-methylenedioxyphenylcarbonyloxy lower alkyl group;

$R_2$ represents hydrogen, a lower alkyl, lower alkoxy, lower alkenyl, amino, or nitro;

$R_3$ and $R_4$, which are identical to or different from each other, represent hydrogen, halogen, cyano, nitro, lower alkyl, or lower alkoxy group; and n represents 0 or 1.

15. A method for the prevention of peptic ulcers in mammals, which comprises administering to a host of a preventively effective amount of an N-acylpiperazine compound or a pharmacologically acceptable salt thereof having a formula:

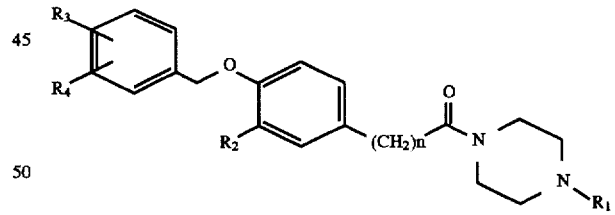

wherein $R_1$ represents a lower alkyl, hydroxy lower alkyl, lower acyl, phenylcarbonyloxy lower alkyl, or 3,4-methylenedioxyphenylcarbonyloxy lower alkyl group;

$R_2$ represents hydrogen, lower alkyl, lower alkoxy, lower alkenyl, amino, or nitro;

$R_3$ and $R_4$, which are identical to or different from each other, represent hydrogen, halogen, cyano, nitro, lower alkyl, or lower alkoxy; and n represents 0 or 1.

16. A method according to claim 15, wherein said peptic ulcers are gastric ulcers in man.

17. The method for treating peptic ulcers according to claim 11, wherein $R_2$ represents a lower alkyl, lower alkoxy, lower alkenyl, amino, or nitro.

18. The method for treatment peptic ulcers according to claim 11, wherein $R_3$ and $R_4$ are not hydrogen at the same time.

19. The method for inhibiting acid secretion in stomach according to claim 13, wherein $R_2$ represents a lower alkyl, lower alkoxy, lower alkenyl, amino, or nitro.

20. The method for inhibiting acid secretion in stomach of mammals according to claim 13, wherein $R_3$ and $R_4$ are not hydrogen at the same time.

21. The method for inhibiting growth of *Helicobacter pyroli* in stomach according to claim 14, wherein $R_2$ represents a lower alkyl, lower alkoxy, lower alkenyl, amino, or nitro.

22. The method for inhibiting growth of *Helicobacter pyroli* in stomach according to claim 14, wherein $R_3$ and $R_4$ are not hydrogen at the same time.

23. The method for the prevention of peptic ulcers according to claim 15, wherein $R_2$ represents a lower alkyl, lower alkoxy, lower alkenyl, amino, or nitro.

24. The method for the prevention of peptic ulcers according to claim 15, wherein $R_3$ and $R_4$ are not hydrogen at the same time.

* * * * *